United States Patent
Miyamoto et al.

(10) Patent No.: US 8,450,556 B2
(45) Date of Patent: May 28, 2013

(54) SHAPED SHEET AND ABSORBENT ARTICLE USING THE SAME

(75) Inventors: Takanobu Miyamoto, Tochigi (JP); Takeshi Miyamura, Tochigi (JP); Taeko Kanai, Tochigi (JP); Aya Yoshimoto, Tochigi (JP); Soichi Fujita, Tochigi (JP); Hiromichi Suzuki, Tochigi (JP); Wataru Saka, Tochigi (JP); Shinobu Takei, Tochigi (JP)

(73) Assignee: Kao Corporation, Tokyo (JP)

( * ) Notice: Subject to any disclaimer, the term of this patent is extended or adjusted under 35 U.S.C. 154(b) by 405 days.

(21) Appl. No.: 12/675,500

(22) PCT Filed: Apr. 30, 2008

(86) PCT No.: PCT/JP2008/058268
§ 371 (c)(1),
(2), (4) Date: Feb. 26, 2010

(87) PCT Pub. No.: WO2009/028236
PCT Pub. Date: Mar. 5, 2009

(65) Prior Publication Data
US 2010/0249740 A1    Sep. 30, 2010

(30) Foreign Application Priority Data

| Aug. 28, 2007 | (JP) | 2007-221326 |
| Nov. 2, 2007 | (JP) | 2007-286251 |
| Dec. 28, 2007 | (JP) | 2007-339651 |
| Dec. 28, 2007 | (JP) | 2007-339689 |
| Dec. 28, 2007 | (JP) | 2007-339724 |
| Jan. 31, 2008 | (JP) | 2008-021928 |

(51) Int. Cl.
*A61F 13/20* (2006.01)

(52) U.S. Cl.
USPC ............ 604/380; 604/383; 604/379; 604/384

(58) Field of Classification Search
USPC ................... 604/379, 380, 383, 384
See application file for complete search history.

(56) References Cited

U.S. PATENT DOCUMENTS

| 4,741,941 A | 5/1988 | Englebert et al. |
| 5,449,352 A | 9/1995 | Nishino et al. |

(Continued)

FOREIGN PATENT DOCUMENTS

| EP | 1323400 A2 | 7/2003 |
| EP | 1338262 A1 | 8/2003 |

(Continued)

OTHER PUBLICATIONS

English translation of Written Opinion of the International Searching Authority issued in PCT/JP2008/058268 (Form PCT/ISA/237).

(Continued)

*Primary Examiner* — Lynne Anderson
*Assistant Examiner* — Bradley Philips
(74) *Attorney, Agent, or Firm* — Birch, Stewart, Kolasch & Birch, LLP

(57) ABSTRACT

A shaped sheet, comprising: a plurality of protrusions (3) on one surface side of the shaped sheet formed of fibers; and connecting portions (5) for being barriers and connecting the protrusions (3) to one another, wherein the connecting portion (5) has a fiber density higher than a fiber density of the protrusion (3).

17 Claims, 13 Drawing Sheets

U.S. PATENT DOCUMENTS

| | | | |
|---|---|---|---|
| 6,090,089 A * | 7/2000 | Tsuji et al. | 604/385.01 |
| 6,436,082 B1 | 8/2002 | Mizutani et al. | |
| 6,803,334 B2 * | 10/2004 | Mizutani et al. | 442/394 |
| 6,926,948 B2 * | 8/2005 | Toyoshima et al. | 428/181 |
| 2002/0058128 A1 | 5/2002 | Toyoshima et al. | |
| 2003/0050615 A1 | 3/2003 | Sakamoto et al. | |
| 2004/0140047 A1 | 7/2004 | Sato et al. | |
| 2008/0114317 A1 * | 5/2008 | Seyler | 604/369 |

FOREIGN PATENT DOCUMENTS

| | | |
|---|---|---|
| EP | 1419754 A1 | 5/2004 |
| JP | 6-277252 A | 10/1994 |
| JP | 7-42057 A | 2/1995 |
| JP | 9-234220 A | 9/1997 |
| JP | 11-347062 A | 12/1999 |
| JP | 2001-137284 A | 5/2001 |
| JP | 2002-165830 A | 6/2002 |
| JP | 2002-345887 A | 12/2002 |
| JP | 2003-126147 A | 5/2003 |
| JP | 2003-275239 A | 9/2003 |
| JP | 2004-113489 A | 4/2004 |
| JP | 2004-174234 A | 6/2004 |
| JP | 2005-245483 A | 9/2005 |
| JP | 2006-305044 A | 11/2006 |
| JP | 2007-167212 A | 7/2007 |

OTHER PUBLICATIONS

Extended European Search Report dated Nov. 8, 2012 for European Application No. 08740936.3.

Japanese Office Action for Application No. 2007-221326 dated Aug. 7, 2012 (with English translation).

Japanese Office Action for Application No. 2007-339651 dated Aug. 7, 2012 (with English translation).

Japanese Office Action for Application No. 2008-106162 dated Jul. 24, 2012 (with English translation).

Japanese Office Action for Application No. 2008-106163 dated Jul. 24, 2012 (with English translation).

Japanese Office Action for Application No. 2008-113703 dated Jul. 24, 2012 (with English translation).

Japanese Information Offer Form dated Jan. 15, 2013 for Japanese Application No. 2008-113703 with English translation.

* cited by examiner

SHAPED SHEET AND ABSORBENT ARTICLE USING THE SAME

TECHNICAL FIELD

The present invention relates to a shaped sheet and an absorbent article using the same.

BACKGROUND ART

Shaped sheets are applied to some absorbent articles, such as sanitary napkins, panty liners, and disposable diapers. For example, as a topsheet, there has been disclosed one in which heat embossing is performed on the surface of a sheet-like hydrophilically treated conjugate fiber non-woven fabric to form protrusions and recesses thereon, and in which the tip surface portions of the protrusions are formed into films, thus providing truncated-cone-shaped protrusions (see Patent Document 1). In this topsheet, the protrusions are independent from one another, and the tip portions of the protrusions are formed into films, resulting in a very high fiber density.

Further, it has been disclosed to join two non-woven sheets together with a plurality of intermittently provided pin embosses, and selectively contract the lower sheet by heat drying to separate the upper sheet in a corrugated fashion, thereby to prepare a top sheet (see Patent Document 2). Further, there has been disclosed an absorbent article which is equipped with a liquid permeable surface sheet, a liquid impermeable back sheet, and a liquid retaining absorbent member provided between the two sheets, and whose surface to be brought into contact with the skin has a bumpy (asperity) region in which a plurality of protrusions are formed in a regular fashion. Further, this absorbent article has a non-bumpy region in which protrusions lower than those of the bumpy region are formed or in which no protrusions are formed (see Patent Document 3). In this absorbent article, the bumpy region is formed by a laminate sheet in which a first layer arranged on the skin side and a second layer on the absorbent member side are stacked, thereby to form a joint portion partially bonding the two layers in a predetermined pattern at the joint portion. Further, the plurality of protrusions in the bumpy region are formed through deformation of the portion of the first layer other than the joint portion into a convex configuration through contraction of the second layer. In the topsheets of Patent Document 2 and Patent Document 3, the protrusions and recesses of the upper layer are formed through contraction of the lower layer, so the fiber density of the upper layer is uniform.

Apart from this, there has been disclosed a topsheet including an upper sheet and a lower sheet and having hollow protrusions, with the bottom portions of the protrusions being rectangular and the protrusions as a whole being formed as rectangular parallelepipeds or truncated tetragonal pyramids (see Patent Document 4).

[Patent Document 1] JP-A-11-347062 ("JP-A" means unexamined published Japanese patent application)
[Patent Document 2] JP-A-2002-165830
[Patent Document 3] JP-A-2003-275239
[Patent Document 4] JP-A-2004-174234

DISCLOSURE OF THE INVENTION

A shaped sheet according to the present invention, has: a plurality of protrusions on one surface side of the shaped sheet formed of fibers; and connecting portions for being a barrier and connecting the protrusions to one another, wherein the connecting portion has a fiber density higher than a fiber density of the protrusion.

Further, an absorbent article according to the present invention, has the shaped sheet located near at least an excretion region, with the surface provided with the protrusions directed toward a skin surface side.

BRIEF DESCRIPTION OF THE DRAWINGS

FIG. 6-1 is an explanatory process view for illustrating a shaped sheet manufacturing method according to an embodiment of the present invention.

FIG. 6-2 is an explanatory process view for illustrating a shaped sheet manufacturing method according to another embodiment.

FIG. 6-3 is a pattern chart illustrating the arrangement of tooth ends when teeth of a first roll and a second roll are engaged with each other.

FIG. 6-4 is an enlarged schematic perspective view of a main portion of a first roll according to an embodiment.

FIG. 6-5 is an enlarged schematic perspective view of a main portion of a first roll according to another embodiment.

Other and further features and advantages of the invention will appear more fully from the following description, appropriately referring to the accompanying drawings.

DETAILED DESCRIPTION OF THE INVENTION

In the following, preferred embodiments of the present invention are described in detail with reference to the accompanying drawings.

Figure 1:
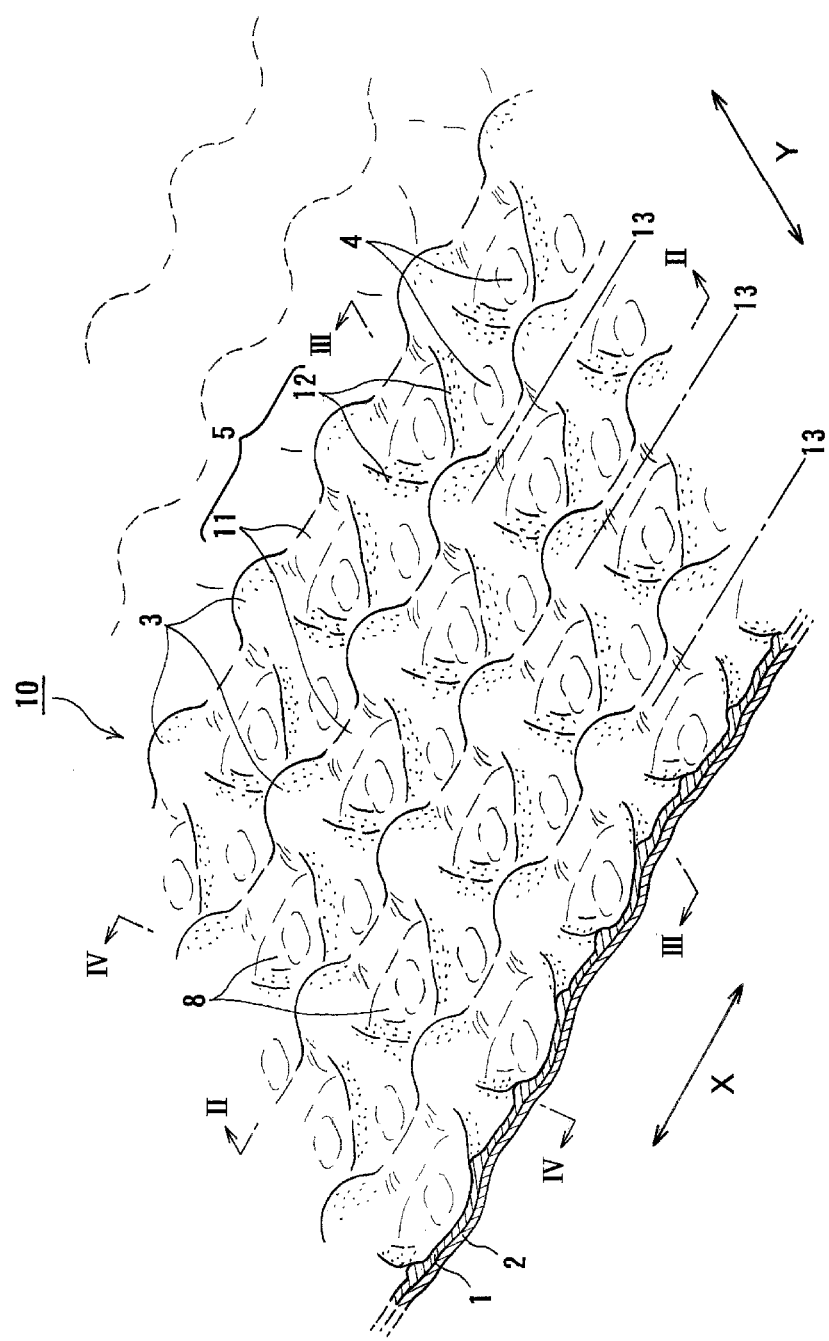
FIG. 1 is a schematic perspective view, partially in section, of a main portion of a topsheet in a shaped sheet according to an embodiment (First Embodiment) of the present invention.
Figure 2:
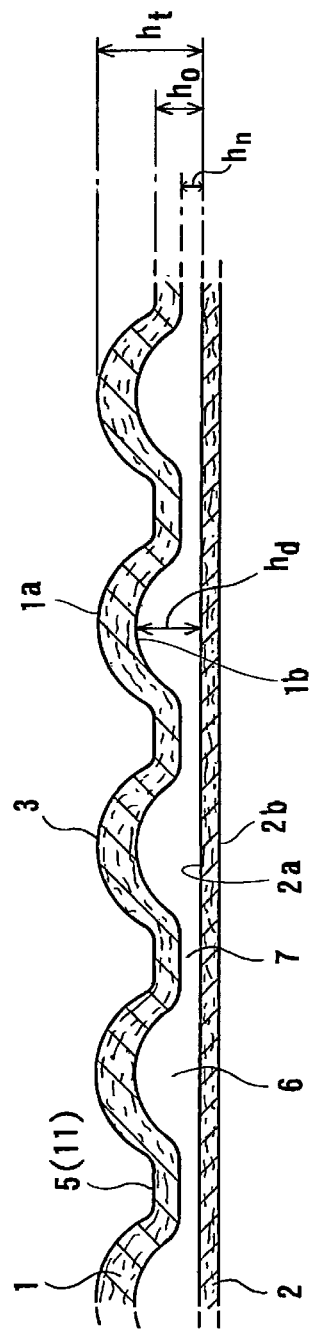
FIG. 2 is an enlarged sectional view, taken along the line II-II, of the shaped sheet of FIG. 1.
Figure 3:
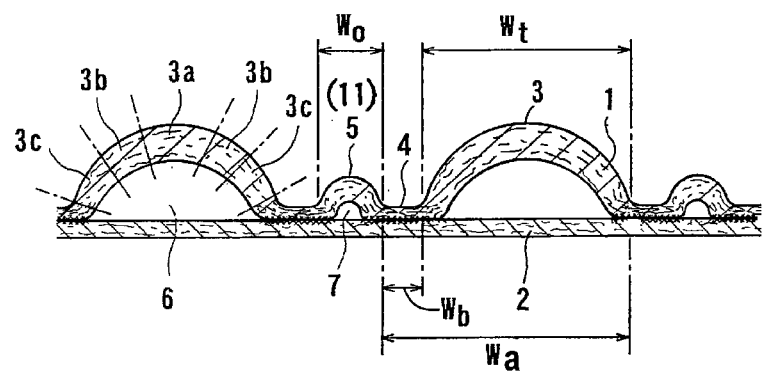
FIG. 3 is an enlarged sectional view, taken along the line III-III, of the shaped sheet of FIG. 1.
Figure 4:
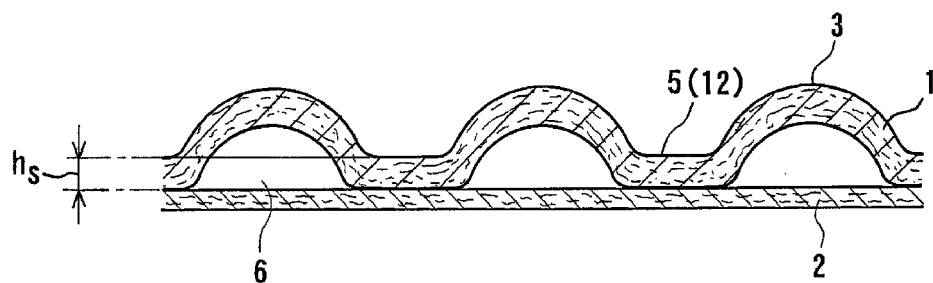
FIG. 4 is an enlarged sectional view, taken along the line IV-IV, of the shaped sheet of FIG. 1.

FIG. 1 is a schematic perspective view of a main portion of a topsheet of an absorbent article that is a shaped sheet according to a preferred embodiment (First Embodiment) of the present invention. FIG. 2 is a sectional view, taken along the line II-II, of the shaped sheet of FIG. 1. FIG. 3 is a sectional view, taken along the line III-III, of the shaped sheet of FIG. 1. FIG. 4 is a sectional view, taken along the line IV-IV, of the shaped sheet of FIG. 1. The following description of the shaped sheet of the present invention centers on the mode in which the shaped sheet is used, with the upper layer sheet side surface of the topsheet illustrated in the drawings facing the skin surface of the wearer, but the invention should not be construed restrictively by those.

A topsheet 10 according to the First Embodiment has an upper layer sheet 1 and a lower layer sheet 2. The topsheet 10 is preferably applied, for example, to an absorbent article, such as a sanitary napkin or a disposable diaper. The topsheet 10 can be used, with an absorbent member (not shown) disposed on the lower surface 2b side of the lower layer sheet 2, and the upper surface 1a side of the upper layer sheet 1 being directly applied to the skin of the wearer.

On the upper layer sheet 1 side of the topsheet 10 of the absorbent article of the First Embodiment, i.e., on the side held in contact with the skin of the wearer, there are formed a plurality of protrusions 3 in a staggered manner (in a zigzag fashion). Any adjacent two protrusions 3 arranged in a staggered manner are connected together by a connecting portion 5 for being a barrier (a first connecting portion 11 and a second connecting portion 12). While in the sectional view of FIG. 2 the upper layer sheet 1 and the lower layer sheet 2 are not bonded together, the two sheets are bonded together by recesses 4 located in front of and behind the drawing plane (see also FIGS. 3 and 4). In FIGS. 2 to 4, FIGS. 8, 9, and 13 discussed below, the depiction of the configuration in the depth direction of the drawings is omitted so as to avoid complication of the drawings. Further, in the present invention, the thickness of each sheet, the size of the structure portion, and the relationship thereamong are not restricted to those illustrated in the drawings.

In this embodiment, the protrusions 3 and the first connecting portions 11 connected together are provided in a plurality of linear protrusion rows 13 (see FIG. 1). The protrusion rows 13 lie in parallel, and broken-line-shaped (or bent-line-shaped) groove portions 8 having recesses 4 and second connecting portions 12 are formed as sandwiched between the protrusions 3 and the first connection portions 11. (In the present invention, regions where no protrusions and no first connecting portions are present are referred to as groove portions. In a topsheet 20 according to another embodiment described below, the recesses 4 themselves constitute the groove portions 8.) The protrusions 3 contain dome-shaped spaces 6 therein. The recesses 4 are arranged among the plurality of protrusions 3 so as to avoid the above-mentioned connecting portions 5 for being barriers. It is only necessary for the plurality of protrusions to be arranged such that the resultant shaped sheet has a three-dimensional convexo-concave form and the three-dimensional shaped sheet exhibits a desired function, and there are no particular limitations regarding the specific number, density, or distribution of the protrusions in the sheet.

As described above, in the topsheet 10 of this embodiment, the mountain-chain-like protrusion rows 13 formed by the protrusions 13 and the first connecting portions 11 are provided in parallel through the intermediation of the gently curved valley-like groove portions 8 (see FIG. 1). The surfaces of the groove portions are not flat but exhibit an undulated surface configuration with the second connecting portions 12 continuous with the adjacent protrusions 3. Due to its particular outer surface configuration formed by the protrusions 3, the recesses 4, the connecting portions 5 for being barriers (first connecting portions 11 and second connecting portions 12), and the groove portions 8, the surface sheet 10 of this embodiment exhibits a high leakage prevention property in the plane (surface) direction, not allowing excretion, such as urine, loose feces (soft stool), menstrual blood, or vaginal discharge, to spread easily. More specifically, in the case of a sheet in which protrusions are simply arranged, when a liquid or semi-solid substance is excreted on the skin surface side of the topsheet 10, the excreted liquid or the like gets around the protrusions due to its fluidity to spread widely over the upper surface of the sheet. However, in the topsheet 10 of this embodiment, there are arranged in parallel the mountain-chain-like protrusion rows 13 in which the protrusions 3 are connected together via the first connecting portions 11, so it is possible to cut off quite effectively the movement of the excreted liquid or the like in the direction orthogonal to the protrusion rows 13. Further, also regarding diffusion of the excreted liquid or the like in the direction parallel to the protrusion rows 13, the undulation in the groove portions 8 due to the above-mentioned recesses 4 and the second connecting portions 12 constitutes an obstruction to the movement, making it possible to effectively suppress liquid spreading that would lead to leakage.

The above-mentioned difference in diffusion prevention property for the excreted liquid or the like in the direction parallel to the direction orthogonal to the protrusion rows 13 may be effectively adjusted according to the function required of the absorbent article. For example, when, in the case of a sanitary napkin or the like, in which the leakage prevention property in the transverse (width) direction is of higher importance than that in the longitudinal direction, the topsheet 10 is oriented so that the protrusion rows 13 extend in the longitudinal direction of the napkin, making it possible to reliably prevent lateral leakage of menstrual blood or the like. Further, menstrual blood or the like is allowed to move to a suitable degree in the longitudinal direction, making it possible to utilize widely and effectively the liquid absorption region of the absorbent member disposed underneath.

The protrusions of the topsheet 10 of the First Embodiment retain the spaces 6 therein. These inner spaces are defined as recessed spaces formed on the back side of the protrusions, and it is preferable that the spaces are ones formed with a functional distance maintained between the lower surface 1b of the upper layer sheet 1 and the upper surface 2a of the lower layer sheet 2. While there are no particular limitations regarding the maximum distance $h_d$ of the inner spaces 6 measured from the upper surface 2a of the lower layer sheet 2, the distance is preferably in the range of 0.4 to 2.8 mm. In the case in which the topsheet is formed solely by the upper layer sheet, the distance $h_d$ may not be one measured from the lower layer sheet but one measured between, for example, the skin side surface of the absorbent member and the lower surface 1b of the upper layer sheet. In the topsheet 10 of this embodiment, when a semi-solid substance, such as loose feces, is excreted on the outer surface of the topsheet, the substance is likely to be taken into the inner spaces 6 through the protrusions 3 of low fiber density. Further, the substance moves to the bottoms of the groove portions 8 and the recesses 4 to remain there whereafter the loose feces or the like is taken into the inner spaces 6 while passing between the fibers of the upper layer sheet 1. Here, the water in the loose feces or the like accommodated in the inner spaces 6 is gradually carried away by the absorbent member or the like arranged underneath the topsheet, and is not allowed to go back, with the result that the loose feces is dried up and solidified. Due to this function, in the topsheet 10 of this embodiment, even when there exists a highly viscous liquid or semi-solid excreted substance contained in loose feces or vaginal discharge, it is possible to maintain a very satisfactory wear feel and a clean skin condition for a long period of time. Further, since it is possible to suppress backward flow of loose feces or the like, mothers are spared from the trouble to wipe away the loose feces from the buttocks of the baby, thereby saving the time period and effort required for diaper changing. For babies, too, the damage to their skin is lessened.

In the topsheet 10 of the First Embodiment, while there are no particular limitations regarding the height $h_t$ of the protrusions 3, the height is preferably in the range of 0.6 to 3.0 mm. Further, in this embodiment, the height $h_o$ of the first connecting portions 11 is smaller than the height $h_t$ of the protrusions, and the ratio of the height of the first connecting portions 11 to the height of the protrusions 3 ($h_o/h_t$) is preferably in the range of 0.3 to 0.8 (see FIG. 2). In the present invention, there are no particular limitations regarding the configuration of the connecting portions 5 for being barriers (first connecting portions 11 and second connecting portion 12) so long as they are of a configuration exhibiting a function to retain excreted liquid or the like to some degree and prevent the movement thereof, and their sectional configuration need not be rectangular but may, for example, be a rounded projecting configuration as in this embodiment (see FIGS. 1 and 3).

Further, in the First Embodiment, the height $h_s$ of the second connecting portions 12 is smaller than the height $h_o$ of the first connecting portions 11, and the ratio ($h_s/h_o$) is preferably in the range of 0.2 to 0.9 (see FIGS. 2 and 4).

The configuration of the protrusions 3 in the First Embodiment will be described in detail. Each protrusion 3 can be functionally divided into an apex portion 3a, a shoulder portion 3b, and a side portion 3c (see FIG. 3). The protrusion 3 exhibits a rounded dome-shaped configuration extending from the apex portion 3a down to the side portion 3c via the shoulder portion 3b. In this way, the protrusions have a rounded configuration, whereby, even when the absorbent article is somewhat shifted due to movement or the like of the wearer, rubbing feel with respect to the skin is suppressed, thus providing a smooth feel. In particular, since each protrusion is curved gently from the shoulder portion 3b toward the apex portion 3a, the contact area between the absorbent article and the skin of the wearer is reduced. By thus reducing the contact area between the topsheet and the wearer, it is possible to substantially reduce sticky feel due to surface contact of the sheet once it has absorbed liquid, thus realizing a fairly dry condition. Further, it exhibits a soft and smooth appearance, and gives a refined impression. The above-mentioned softness, smoothness, and dry feel (free from viscosity or sticky feel owing to the dry surface) of the topsheet, and the satisfactory appearance giving such an impression cannot be easily obtained from a sheet in which the protrusions are basically formed as rectangular parallelepipeds or truncated tetragonal pyramid or cones. Further, in the topsheet 10 of this embodiment, the protrusions 3 contain the spaces 6 retaining air, so it is possible to obtain a distinctive cushion property and to realize a yet softer feel.

In the First Embodiment, the side portion 3c of each protrusion 3 is disposed below the approximate intermediate point of the height $h_t$ of the protrusion (i.e., on the side opposite to the skin). The side portion 3c of the protrusion is at a position corresponding to the skirts of the protrusion leading down to the surface of the groove portion and the recess and viscous liquid or semi-solid substance such as loose feces temporarily collects around this portion. In this regard, it is preferable to lower the fiber density of the side portion 3c of the protrusion and to provide slits or thin portions therein since that allows the highly viscous liquid or the like to pass effectively therethrough to be quickly accommodated and concealed in the inner spaces 6 of the protrusions.

The topsheet of this embodiment includes the upper layer sheet 1 having the protrusions 3, and the flat lower layer sheet 2 disposed on the side opposite to the surface where the protrusions 3 are present and the upper layer sheet 1 and the lower layer sheet 2 are bonded together via at least a part of the recesses 4 of the upper layer sheet by embossing. However, there are no particular limitations regarding the bonding method, and it is also possible to adopt some other bonding method. In the present invention, when it is said that a sheet is "flat", it means the sheet as a whole is substantially flat, with no shaping being performed thereon to form protrusions, and there may be some protrusions and recesses due to bonding with another sheet material or some inevitable surface bumpiness due to sheet forming. In contrast, when it is said that a sheet is shaped, it means that the sheet is not flat, and, for example, it means that the sheet surface of natural configuration is undulated to such a degree that the shadows of the protrusions can be visually observed under irradiation with light from a predetermined direction.

While there are no particular limitations regarding the width $w_b$ of the recesses, it is preferable that, assuming the distance between adjacent structures to be $w_a$, the ratio of the width $w_b$ of the recess to this distance $w_a$ ($w_b/w_a$) is in the range of 0.1 to 0.7. Taking into consideration the relationship with the dimensions of an ordinary absorbent article, the specific recess width $w_b$ that can be practically adopted is in the range of 0.5 to 2.0 mm. In the topsheet of this embodiment, the width $w_o$ of the first connecting portions 11 (width in the direction orthogonal to the connecting direction) is smaller than the width $w_t$ of the protrusions 3 and, for example, the ratio of the width $w_o$ of the first connecting portions 11 to the width $w_t$ of the protrusions 3 ($w_o/w_t$) is preferably in the range of 0.2 to 0.8. This preferable range of the width also applies to the ratio ($w_s/w_t$) of the width $w_s$ of the second connecting portions (width orthogonal to the connecting direction) (not shown). It is practical for the specific width $w_t$ of the protrusions 3 to be in the range of 2 to 6 mm.

In the topsheet 10 of this embodiment, the second connecting portions 12 are disposed in the groove portions 8 (see FIGS. 1 and 4). In this embodiment, while the lower surfaces of the second connecting portions 12 of the upper layer sheet 1 are in contact with the lower layer sheet 2, they are not bonded thereto by embossing. In this regard, in this embodiment, there are tunnel-like spaces 7 in the inside of the first connecting portions 11, whereby the inner spaces 6 of the protrusions 3 are connected together, but the tunnel-like spaces 7 may be omitted (see FIG. 3). In this way, among the protrusions 3 arranged in a staggered manner, there are arranged the first connecting portions 11 and the second connecting portions 12 differing in height and width and in the way in which the inner spaces are joined together. Thus, it is possible to obtain a leakage prevention property which cannot be attained by simply forming protrusions, as stated in the above.

Further, by thus arranging portions differing in sheet thickness in the form of a network, the topsheet 10 of this embodiment can provide a draping property (property allowing the sheet to be fitted even to a skin surface with complicated undulation by being gently deformed without involving any buckling, making it possible for the sheet to conform to any change in skin undulation due to movement or the like of the wearer). As a result, the sheet surface gently conforms to a skin surface with a complicated undulation, and it is possible to maintain the conformity even if the surface undulated configuration changes. For example, even when the absorbent article is held in contact with a portion with great skin undulation as in the case of a crotch portion, the topsheet 10 can be fitted to the skin without involving any gap therebetween. Further, even when the skin undulation continues to change due to movement or the like of the wearer, the topsheet is deformed in conformity with the change in the undulation, making it possible to maintain a satisfactory fitting property.

In the topsheet 10 of this embodiment, the fiber density $D_o$ of the connecting portions 5 for being barriers (first connecting portions 11 and second connecting portions 12) is higher than the fiber density $D_t$ of the protrusions. Further, the fiber density $D_b$ of the recesses 4 is higher than the fiber density $D_o$ of the connecting portions 5 for being barriers.

In the present invention, the "fiber density" of each portion is calculated by observing the unit area of the apex portion of each portion with an optical microscope in a state in which there is no change in configuration (for example, in a noncontact state in which no load is applied), and measuring the number of fibers in a predetermined sheet portion (which is the upper layer sheet in this embodiment) or in the sheet surface.

The ratio of the fiber density $D_t$ of the protrusions to the fiber density $D_o$ of the connecting portions 5 for being barriers, $D_t/D_o$, is preferably in the range of 0.8 to 0.3. Further, the ratio of the fiber density $D_o$ of the connecting portions 5 for being barriers to the fiber density $D_b$ of the recesses 4, $D_o/D_b$, is preferably in the range of 0.6 to 0.1. When there is a difference between the density $D_{o2}$ of the first connecting portions 11 and the density $D_{o2}$ of the second connecting portions 12, the fiber density $D_o$ of the connecting portions 5 for being barriers refers to the average value of the two. In this embodiment, the density $D_{o1}$ of the first connecting portions is preferably lower than the density $D_{o2}$ of the second connecting portions.

By thus providing a gradient in fiber density in each structural portion in the topsheet 10, it is possible, for example, to quickly transfer or make a liquid of low viscosity move toward the high fiber density side, that is, from the protrusions to the recesses 4 and the periphery thereof via the connecting portions. As a result, it is possible to draw in the liquid to the side of the topsheet 10 in noncontact with the skin, and to quickly transfer the liquid to the absorbent member provided underneath, causing it to be absorbed and retained. In contrast, regarding a highly viscous liquid or semi-solid substance such as loose feces, it is likely to be permeated through the portions around the apexes of the protrusions 3 formed as large domes due to their low density, thus enhancing the effect by which it is accommodated in the spaces 6. In this way, the liquid drawing-in property as indicated by the gradient in fiber density and the leakage/backward-flow prevention property due to the distinctive topsheet configuration, are exerted simultaneously, so even when excrete substances differing in viscosity coexist, it is possible to properly absorb and retain them. Further, since the fiber density of the protrusions 3, which are directly brought into contact with the skin, is low, the excreted substance, such as urine or loose feces, does not easily remain among the fibers. As a result, remaining of liquid on the surface and stickiness are effectively suppressed, making it possible to obtain an especially dry feel due to the apexes 3a of the protrusions brought into contact with the skin. Further, it is possible to maintain the user's skin in a clean state, making it possible to protect the skin of an infant or a woman from rash or the like.

As described above, in the topsheet 10 of this embodiment, the protrusions 3 are arranged in a staggered manner. Herein, the term "in a staggered manner (or zigzag fashion)" means a state in which the protrusions 3 in each row are arranged at equal intervals and in which the protrusions of the adjacent rows are offset (preferably by 0.5 pitches). More specifically, it means a state in which, when the protrusions 3 of each row are projected in a direction orthogonal to the row, between the projected images of the protrusions 3 of a specific row (preferably right between), the projected images of the protrusions of the adjacent row are arranged. However, it also includes a case in which there is a slight deviation in the above arrangement, such as a deviation inevitable in terms of production. By thus arranging the protrusions 3 in a staggered manner, it is possible to uniformly disperse the pressure on the skin of the wearer, making it possible to realize a satisfactory cushion property. Further, also from the viewpoint of absorption and retention of liquid, this function is uniformly exerted over the entire sheet, which is preferable.

While the topsheet 10 of this embodiment adopts the double-layer structure including the upper layer sheet 1 and the lower layer sheet 2, it is also possible for the topsheet to be formed solely by the upper layer sheet 1. In this case, it is possible, for example, to stack the topsheet having the upper layer sheet 1 on the upper surface of the absorbent member such that the surface 1b thereof which is not to be brought into contact with the skin is held in contact therewith. In this case, it is also possible to bond the back surface of the topsheet having the upper layer sheet 1 to the upper surface of the absorbent member. By thus adopting a topsheet solely having the upper layer sheet 1, the elasticity and flexibility due to the protrusions 3 arranged on the skin surface side and the spaces 6 corresponding thereto, and further, to the connection of those by the connecting portions 5 for being barriers, can be exerted, as in the case of the double-layered structure described above. Also regarding the permeation treatment function for liquids, loose feces or the like, the workings of the dome-shaped spaces 6 can be exerted through a combination with the absorbent member or the like. At that time, in particular, loose feces or the like concealed inside the spaces 6 is held in direct contact with the absorbent member, so the water contained therein is likely to move to the absorbent member, and the loose feces or the like is advantageously quickly dried. Further, it is also advantageous in that the liquid transferred to the connecting portions 5 for being barriers and the recesses 4, whose fiber density is higher than that of the protrusion apexes 3a, are directly absorbed and retained by the absorbent member, without passing through the lower layer sheet 2.

Figure 5:
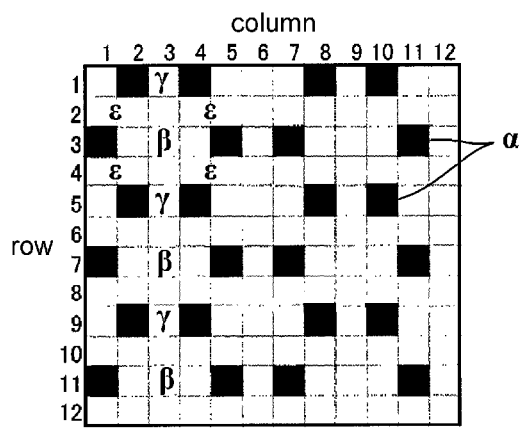
FIG. 5 is a pattern chart that depicts a six-point embossing pattern in a coordinate system.

FIG. 5 is a schematic pattern chart illustrating the arrangement of a six-point emboss a when the topsheet of the First Embodiment is seen in plan view. The drawing illustrates an emboss pattern in a 12 row×12 column square pattern, the components of the six-point emboss pattern being as follows. The six embosses (1, 2), (1, 4), (3, 1), (3, 5), (5, 2), and (5, 4) constitute a first six pattern element (first element). Here, the values in the parentheses indicate (row number, column number). The adjacent second element on the right-hand side is formed by the six embosses (1, 8), (1, 10), (3, 7), (3, 11), (5, 8), and (5, 10). Further, the third element below the first element shares the two points (5, 2) and (5, 4) with the first element. It is formed by the six points of (5, 2), (5, 4), (7, 1), (7, 5), (9, 2), and (9, 4). Further, the fourth element on the right-hand side thereof shares the embosses (3, 5), (3, 7), (5, 4), (7, 5), and (5, 8) with one or another of the first through third elements, and includes six points having emboss (7, 7)

and the above-mentioned five points. In this way, six-point patterns are repeatedly formed while sharing a part of the elements (at least two points).

Here, when the above six-point emboss pattern is applied to the form of the topsheet 10, the embosses a constitute the recesses 4. Further, as regards the first element, the central point β thereof constitutes the protrusion 3 (protrusion apex 3a), and the first connecting portions 11 are disposed at positions γ in front of and behind the same. At this time, the second connecting portions 12 are disposed at positions c. Further, the protrusion 3 is also disposed at the position γ at the center of the third element, and is connected to the protrusion 3 of the first element through the first connecting portions 11 formed at the positions γ. As a result, the column extending at the column 3 (coordinate) formed by the positions β and γ constitutes a protrusion row 13 in the topsheet 10. Similar protrusions rows 13 are repeated at column 6 (coordinate), column 9 (coordinate), . . . , and the protrusions 3 spread out in a plane direction in a staggered manner, further forming the topsheet 10 of a distinctive surface configuration having the connecting portions 5 for being barriers and the recesses 4. In this way, in the First Embodiment, the upper layer sheet 1 and the lower layer sheet 2 are bonded together in a six-point seal pattern having six-point bonding portions, with each bonding unit sharing at least two points with the adjacent bonding units, and with each protrusion 3 being formed so as to be surrounded by six-point bonding portions constituting bonding units.

In the topsheet 10 for the absorbent article of the First Embodiment, there are no particular limitations regarding the fibers constituting the upper layer sheet 1 or the lower layer sheet 2. For example, it is preferable to adopt fibers of 1.0 to 7.8 dtex. While in this embodiment each of the upper layer sheet 1 and the upper layer sheet 2 is of a one-layer structure, it is also possible to adopt a structure of two layers or more. Further, it is also possible to provide a layer of some other function between and/or outside the layers. While there are no particular limitations regarding the basis weight of the upper layer sheet 1 and the lower sheet 2, taking into consideration of the fact that they are applied to an ordinary absorbent article, it is advisable from the practical viewpoint for the basis weight of the upper layer sheet 1 and the lower layer sheet 2 to be in the range of 10 to 40 g/m$^2$.

It is preferable to use non-woven fabric for the upper layer sheet 1 and the lower layer sheet 2. As the non-woven fabric, it is possible to use an ordinary non-woven fabric. Examples of the non-woven fabric include a thermal bond non-woven fabric manufactured by a card method, a spun bond non-woven fabric, a melt blown non-woven fabric, a spunlace non-woven fabric, and a needle punch non-woven fabric. When bonding the upper layer sheet 1 and the lower layer sheet 2 by heat fusion-bonding as described below, the non-woven fabric preferably contains a heat fusion-bonding fiber. The heat fusion-bonding fiber is preferably of a sheath/core structure, such as PET/PE or PP/PE. Further, it is preferable to subject the no-woven fabric to hydrophilic treatment using a surface active agent or the like. Among the kinds of fibers of the upper layer sheet 1 and lower layer sheet 2, a preferable combination is one of PET/PE fibers.

Figures 1, 6:
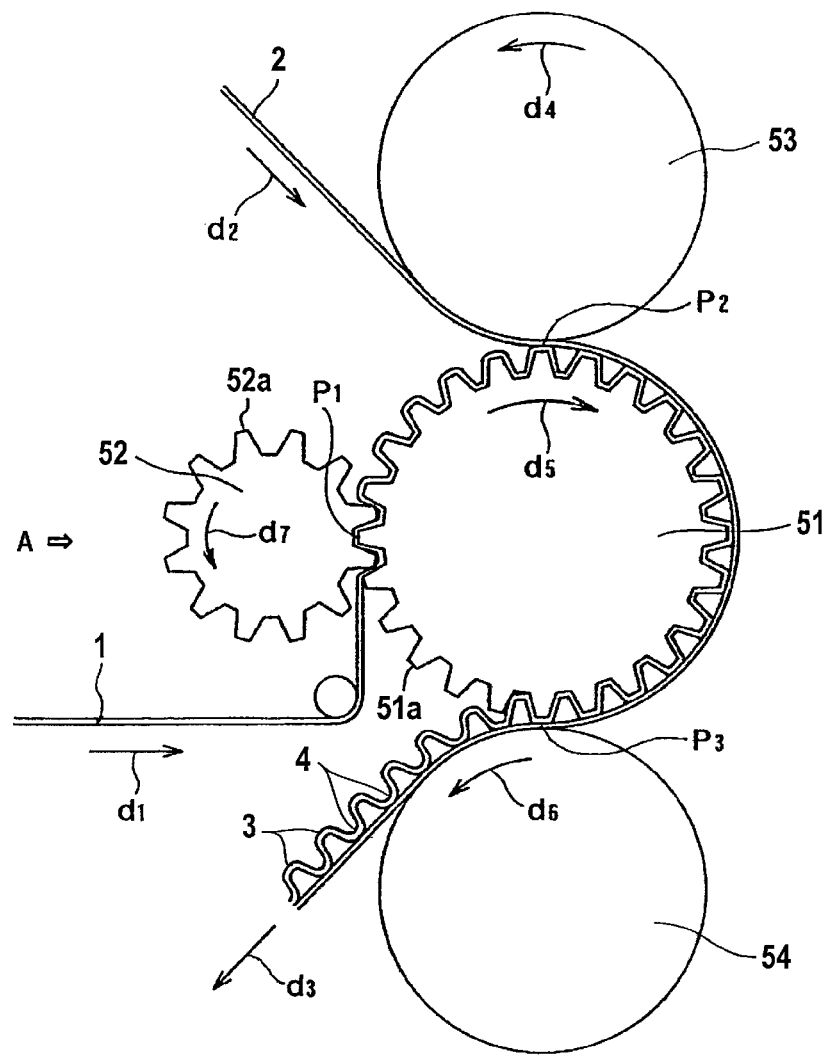
Figures 2, 6:
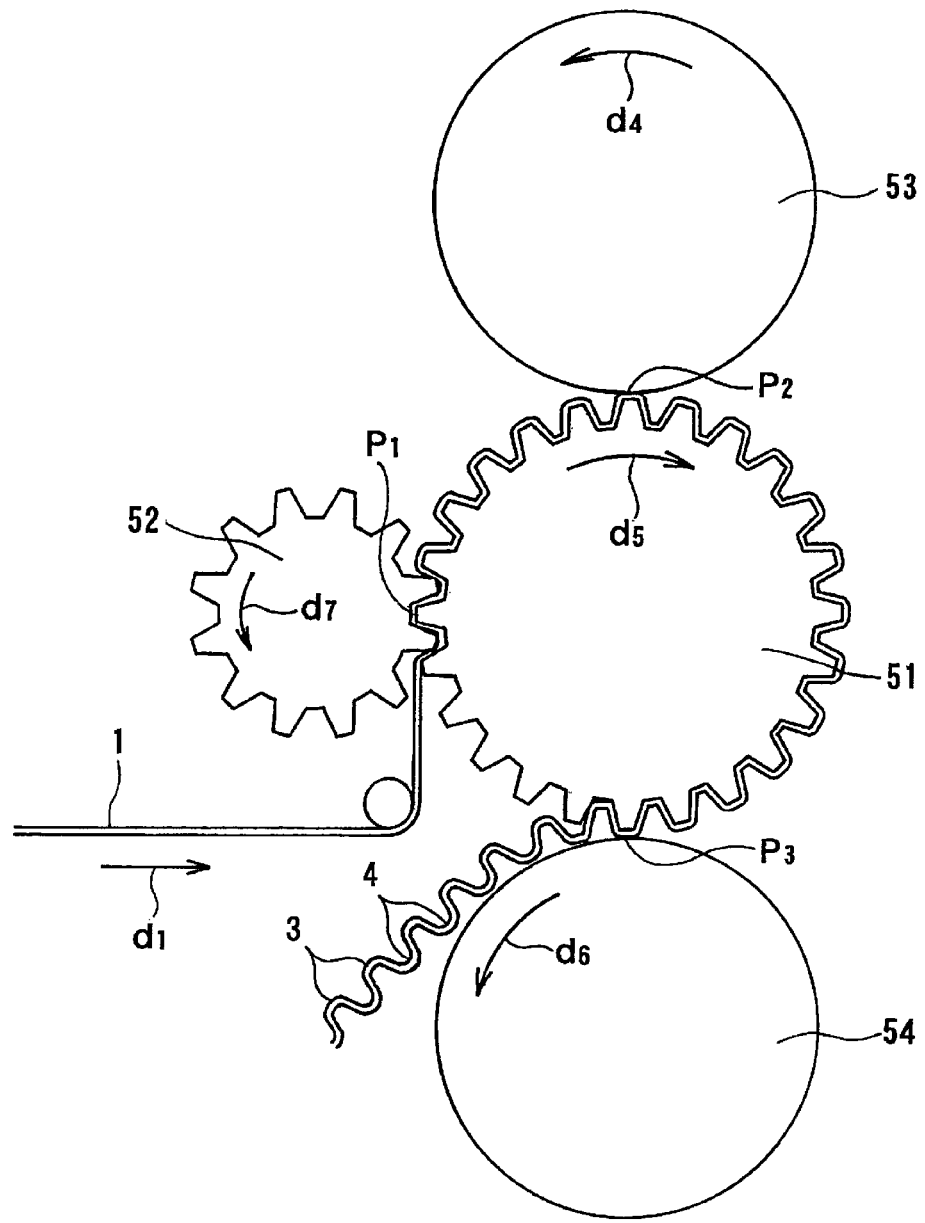
Figures 3, 6:
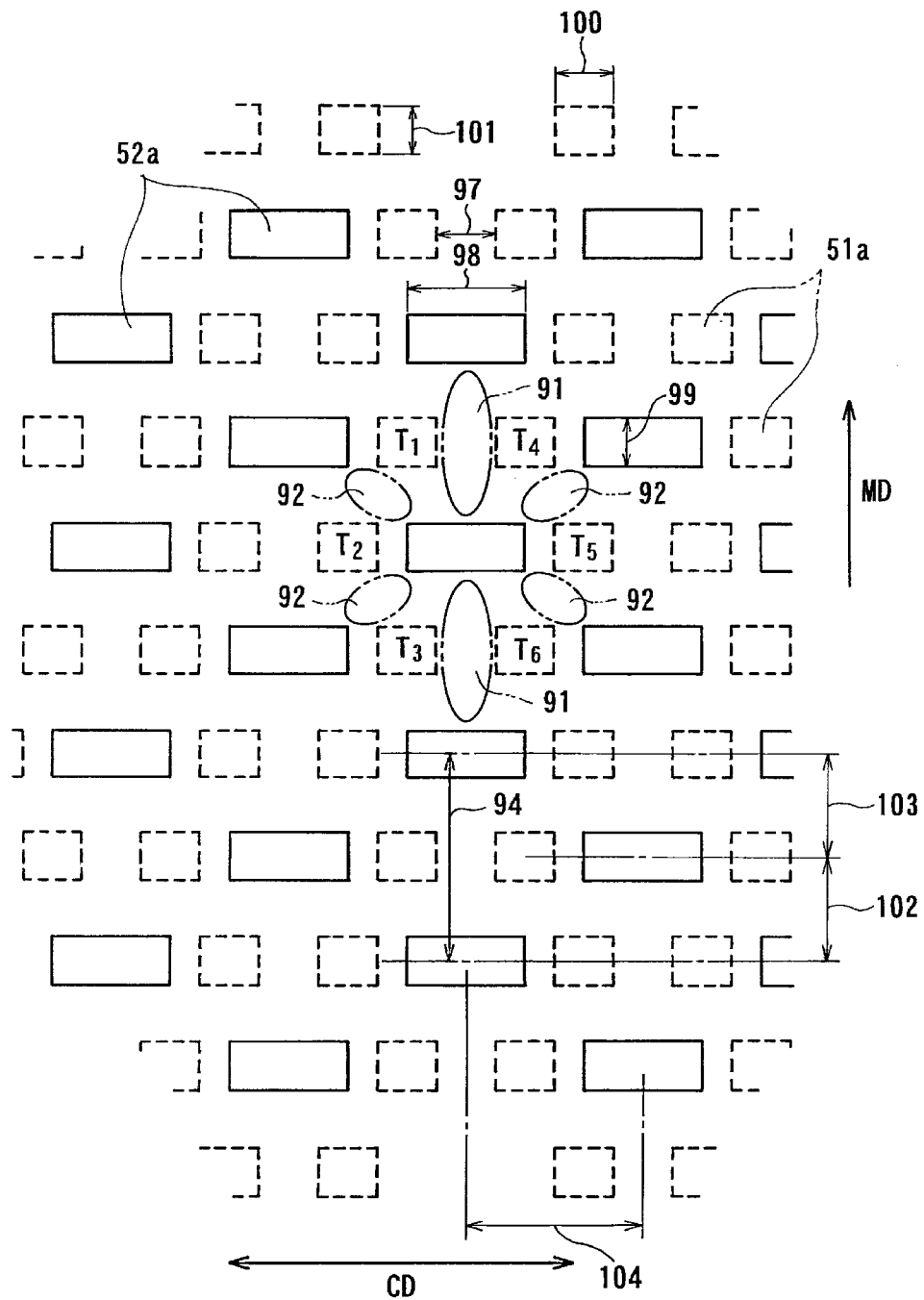
Figures 4, 6:
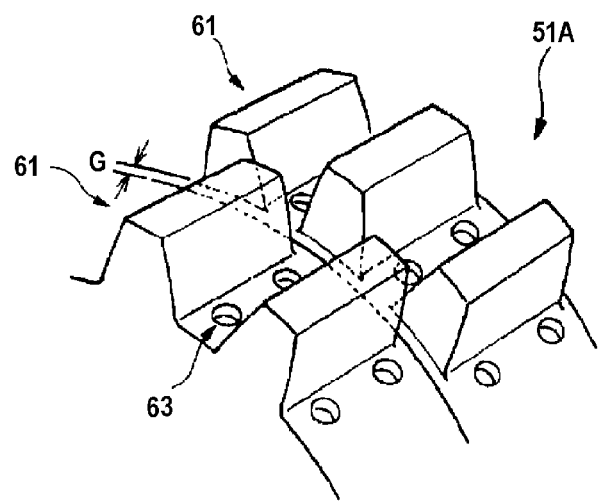
Figures 5, 6:
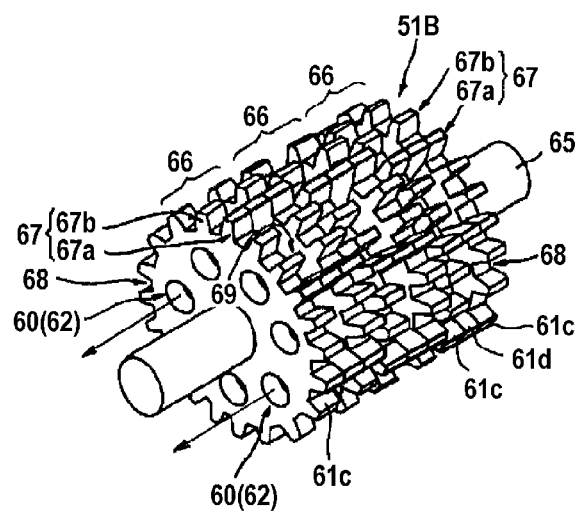

Next, a preferable method of manufacturing the topsheet 10 for an absorbent article according to this embodiment preferable as the shaped sheet of the present invention will be described with reference to the drawings. FIG. 6-1 is a schematic explanatory view illustrating a mode of manufacturing process for the topsheet 10 of the First Embodiment. As illustrated in the drawing, first, the upper layer sheet 1 is paid out from a raw fabric roll (not shown), and apart from this, the lower layer sheet 2 is paid out from a raw fabric roll (not shown). The upper layer sheet 1 and the lower layer sheet 2 are respectively paid out in the MD directions thereof (directions d1 and d2). Herein, the term MD direction refers to the direction in which a sheet material, such as a non-woven fabric, travels at the time of production. The term MD direction is an abbreviation of "machine direction" and is sometimes simply expressed as MD to indicate the direction. On the other hand, the term CD direction indicates a direction orthogonal to the MD direction. The term CD direction is an abbreviation of "cross direction" and is sometimes simply expressed as CD to indicate the direction.

The paid-out upper layer sheet 1 is engaged in the mesh portion P$_1$ of a first roll 51 with a protrusion/recess peripheral surface and a second roll 52 with a protrusion/recess peripheral surface meshed therewith, thereby shaping the upper layer sheet 1 into a protrusion/recess configuration. It is preferable that the tooth trough portion of each tooth of the first roll 51 has a suction hole (not shown). The tooth trough portions correspond to the recesses of the protrusion/recess peripheral surface configuration of the first roll 51. The suction hole leads to a suction source (not shown) such as a blower or a vacuum pump, and it is preferable that the suction source is controlled such that suction is effected from the mesh portion P$_1$ of the first roll 51 (rotating in the direction indicated by arrow d$_5$) and the second roll 52 (rotating in the direction indicated by arrow d$_7$) to the portion P$_3$ where the topsheet formed by bonding together the upper layer sheet 1 and the lower layer sheet 2 is sent out. A specific example of the suction roll will be described in detail below with reference to FIGS. 6-4 and 6-5. Thus, the resultant upper layer sheet 1 shaped into a protrusion/recess configuration through the engagement of the first roll and the second roll, is maintained in the shaped state while held in intimate contact with the peripheral surface of the first roll 51 by the suction force due to the suction hole. Regarding the rolls 51, 52 having protrusions and recesses on the peripheral surfaces thereof, it is possible to use, for example, the ones illustrated in FIGS. 2 to 5 of JP-A-2004-174234.

At a confluence portion P$_2$, the upper layer sheet 1 is overlaid on the lower layer sheet 2 separately supplied, with the upper layer sheet 1 being held in intimate contact with the peripheral surface of the first roll 51 through suction. Here, it is preferable that the two sheets are pressurized between the first roll 51 and a third roll 53. As the third roll 53, it is preferable to use an anvil roll having no protrusions or recesses, and it is preferable to heat solely the third roll 53 to a predetermined temperature. As a result, the upper layer sheet 1 and the lower layer sheet 2, situated at the distal ends of the teeth of the first roll 51, are joined together by heat fusion-bonding. The recesses 4 are formed upon formation of the topsheet through this press bonding. On the other hand, the upper layer sheet 1 and the lower layer sheet 2 are not pressurized by the recesses of the gear, and undergo no heat fusion-bonding, thereby forming the protrusions 3. That is, in this mode, no press heating treatment by the first roll 51 and the second roll 52 is effected in the sheet shaping, so softness is maintained at the apexes of the protrusions 3. Thus, when used as a topsheet, even though the portions constituting the recesses 4 undergo heat pressing to cause heat fusion of the non-woven fabric fibers, making them somewhat harder, the protrusions 3 protrude in a soft state, so no hard portions are brought into direct contact with the skin, thus realizing a good feel to the skin. Then, the portions constituting the first connecting portions 11 and the second connecting portions 12 are shaped while held between the recesses 4, and the protrusions 3 are arranged so as to be connected together.

In the manufacturing method of this mode, the composite sheet formed by combining the upper layer sheet 1 and the lower layer sheet 2 is heated and pressurized at the portion P$_3$ where it is held between the first roll 51 and a fourth roll 54. At this time, it is preferable that the fourth roll 54 is an anvil roll that, like the third roll 53, has no protrusions or recesses in its outer periphery. It is preferable that the fourth roll 54 is heated to a predetermined temperature. In this way, there is formed a firmly fixed bonding portion, thereby maintaining the shape stability of the protrusions.

FIG. 6-2 is a schematic explanatory view illustrating another mode of manufacturing process for a shaped sheet of the present invention. As illustrated in the drawing, this mode is the same as the mode illustrated in FIG. 6-1 in that the first through fourth rolls (51, 52, 53, 54) are used. However, in the mode illustrated in FIG. 6-2, the lower layer sheet 2 is not used, and solely the upper layer sheet 1 is used. In the upper layer sheet 1, there are formed protrusions and recesses constituting the protrusions 3 and the trough portions 4. Thus, although not connected with another sheet at the trough portions 4, it is heated and pressurized by the first roll 51 and the third roll 53 or the fourth roll 54, and the non-woven fabric fibers are heat-fused and set. In this way, not only is the sheet simply bent into a protruded and recessed configuration, but is shaped so as to constitute the protrusions 3 and the trough portions 4 exhibiting a specific function when formed as the topsheet as described above. Further, the sheet shaping through the tooth engagement of the first roll 51 and the second roll 52 and the suction by the first roll 51 at positions P$_1$ through P$_3$ are the same as those of the mode illustrated in FIG. 6-1.

FIG. 6-3 is a schematic pattern chart illustrating how the teeth of the first roll and the second roll are brought into mesh with each other in the manufacturing method according to the mode illustrated in FIG. 6-1. In FIG. 6-3, the distal ends of the teeth of the two rolls at the point P$_1$ where the teeth of the first roll and the second roll are in mesh with each other are projected from the direction of the arrow A of FIG. 6-1. The solid lines indicate the teeth (the distal ends of the teeth) 52a of the second roll 52, and the dashed lines indicate the teeth (the distal ends of the teeth) 51a of the first roll 51. It should be noted, however, that the two rolls are actually circular in front view (see FIG. 6-1), and mesh with each other with solely one row of teeth, while, in FIG. 6-3, patterning is effected as if teeth on flat opposing plates are in mesh with each other (or feeding is effected in the MD direction, with the engagement at the point P$_1$ being continued in time line).

The above-mentioned tooth engagement of the two rolls will be described in more detail. In the pattern chart of FIG. 6-3, FIG. 6-1 is observed from the direction A, so the distal ends of the teeth 52a retract toward the depth side of the drawing, and the distal ends of the teeth 51a protrude toward the front side of the drawing, with the two being engaged with each other. That is, when the upper layer sheet 1 (see FIG. 6-1) is forced in while retracting the distal ends of the teeth 52a toward the depth side of the drawing, to prepare the topsheet, a number of locally bent portions forming the protrusions 3 (see FIG. 1) are shaped. On the other hand, when the distal ends of the teeth 51a push up the upper layer sheet toward the front side of the drawing, to prepare a topsheet, a number of locally bent portions constituting the trough portions 4 are shaped. The upper layer sheet thus shaped into a protrusion/recess configuration is fed toward the third roll while maintaining the intimate contact with the first roll, and is overlaid on the lower layer sheet 2 fed separately as described above (see FIG. 6-1). Then, the two sheets are heated and pressurized between the distal ends 51a of the teeth of the first roll 51 and the peripheral surface of the third roll 53 or fourth roll 54, forming a heat-fusion-bonded heat emboss with the distal end portions 51a of the teeth.

Here, of the distal end portions 51a of the teeth of FIG. 6-3, solely the distal ends T$_1$ through T$_6$ are discussed. The distal ends of the teeth T$_1$ through T$_6$ form portions constituting the recesses 4. At this time, the portions of the non-woven fabric pushed out (or pushed in) by the distal ends 51a, 52a of the teeth move locally through stretching (or compression), and, while doing so, the fibers situated, for example, at the distal ends, tend to enter the gaps of the teeth of the two rolls. At this time, tension is normally applied to the upper layer sheet 1 in the MD direction, so, due to the influence thereof, a distinctive motion is imparted to the travel of the fibers of the non-woven fabric constituting the upper layer sheet. More specifically, when the fibers tend to enter the gaps between the distal ends of the teeth T$_1$ through T$_6$, due to the sheet tension applied in the MD direction, the fiber travel state differs between the MD direction and the CD direction. That is, in a region 91 constituting the gap between the distal ends of the teeth T$_1$ and T$_4$ and between the distal ends of the teeth T$_3$ and T$_6$, the amount of fibers entering from another region 92 increases, and when formed as a topsheet, there are formed portions constituting the first connecting portions 11. Further, the portion corresponding to the region 91 is not heated and pressurized by the tooth distal end 52a, so the portion is not bonded to the lower layer sheet 2, thus forming the tunnel-like spaces 7 of the topsheet. In FIG. 6-3, the MD direction corresponds to the X-direction in the topsheet of the embodiment illustrated in FIGS. 1 and 2.

In contrast, in the regions 92, the amount of fibers entering is relatively small, with the result that, when formed as the topsheet, they only form the second connecting portions 12 (the small protrusions 9 in the Third Embodiment described below). In this way, the recesses 4 formed by the portions pressurized by the distal ends of the teeth 51a and the second connecting portions 12 constitute continuous broken-line-shaped groove portions. In the specific example illustrated, when formed into groove portions, the row formed by the distal ends of the teeth T$_1$, T$_2$ and T$_3$ and the row formed by the distal ends of the teeth T$_4$, T$_5$ and T$_6$ constitute a groove portion 8 continuous in one broken-line-shaped fashion in the MD direction. Thus, a mountain-chain-like protrusion row 13 in which the protrusions and the first connecting portions of the topsheet are connected in the X-direction in FIG. 1, is formed to extend in the MD direction in the manufacturing method of this mode (see FIG. 6-3). By contrast, the sectional configuration illustrated in FIG. 3 extending in the Y-direction of FIG. 1, is formed in the CD direction of FIG. 6-3.

Here, assuming that the area of the hexagon formed by connecting the centers of T$_1$ through T$_6$ of the first roll teeth (distal end surfaces) 51a is the basic area A, and that the area of the portion contained in the hexagon formed by connecting the centers of T$_1$ through T$_6$ of the first roll teeth 51a is area B, the ratio of the area B to the basic area A (B/A) is preferably in the range of 0.10 to 0.25. When the value of this ratio (B/A) is too small, there is no difference between the protrusions 3 and the first connecting portions 11, so they are formed into one protrusion. Thus, the first connecting portions 11 cannot be formed, so the protrusion is easily crushed. When this ratio (B/A) is too large, the tunnel-like spaces 7 in the first connecting portions 11 may disappear. Further, the ratio of the area C of the second roll teeth (distal end surfaces) 52a within the basic area A to the basic area A (C/A), is preferably in the range of 0.10 to 0.25. When this ratio (C/A) is too small, the formation of the protrusions may become difficult. When this ratio (C/A) is too large, the protrusions are likely to assume a rectangular-parallelepiped-like configuration, and become rather hard, resulting in deterioration in softness to touch. It is preferable that the value obtained by dividing the distance 97 between the first roll teeth by the CD dimension 98 of the second roll teeth is to be in the range of 0.25 to 0.83. By adjusting this value, it is possible to obtain in a still more stable manner the substantially mound-shaped protrusions 3 and the first connecting portions 11.

While there are no particular limitations regarding the MD dimension 101 of the first roll teeth, the dimension is preferably in the range of, for example, 0.5 to 3.5 mm, and more preferably, of 0.6 to 2 mm. Further, while there are no particular limitations regarding the CD dimension 100, it is preferably in the range of, for example, 0.5 to 3.5 mm, and more preferably, of 0.6 to 2 mm. Further, while there are no particular limitations regarding the interval 97 between the first roll teeth, it is preferably in the range of, for example, 0.8 to 5 mm, and more preferably, of 1 to 2 mm. While there are no particular limitations regarding the MD dimension 99 of the second roll teeth, the dimension is preferably in the range of, for example, 0.5 to 3.5 mm, and more preferably, of 0.6 to 2 mm. Further, while there are no limitations regarding the CD dimension 98, it is preferably in the range of, for example, 0.5 to 6 mm, and more preferably, of 0.6 to 4 mm. While the interval 94 between the teeth of the first roll 1 or the second roll 2 may be determined as appropriate, it is preferably in the range of, for example, 1.5 to 10 mm, and more preferably, of 2 to 6 mm. While there are no particular limitations regarding the tooth interval 102 in the MD direction of the first and second rolls, it is preferably in the range of, for example, 0.4 to 4 mm. Also, while there are no particular limitations regarding the tooth interval 103 in the MD direction of the first and second rolls, it is preferable that the tooth interval 103 is the same as the tooth interval 102 in the MD direction of the first and second rolls, more preferable that it is in the range of, for example, 0.4 to 4 mm. Further, there are no particular limitations regarding the tooth interval 104 in the CD direction, it is preferably in the range of, for example, 1.2 to 7.5 mm.

Further, the height and configuration of the teeth of the first and second rolls may be determined as appropriate according to the configuration of the target topsheet. For example, the tooth height is preferably in the range of 0.8 to 9 mm. While in FIG. 6-3 the sheet shaping through engagement of the teeth of the first roll and the second roll is illustrated in relation to the manufacturing method according to the mode illustrated in FIG. 6-1, this also applies to the manufacturing method according to the mode illustrated in FIG. 6-2.

Further, it is preferable to adopt a non-woven fabric of an MD rupture elongation of 100% or more, which makes it possible to form a shaped topsheet of a preferable configuration according to the present invention.

FIG. 6-4 is an enlarged schematic perspective view of a main portion of a first roll 51 according to an embodiment (51A). The first roll 51 is formed as a roll by combining a plurality of spur gears 61, 61, . . . of a predetermined tooth width. It is preferable that the tooth width of each gear is determined according to the distance between the protrusions of a sheet for a desired absorbent article. In this embodiment, the adjacent gears are combined such that their tooth pitches are offset by 0.5 pitch.

Suction holes 63 are formed in the tooth groove (tooth trough) portions of each gear of the first roll 51A. The topsheet is held in intimate contact with the peripheral surface of the first roll by the suction force due to the suction holes 63, thereby maintaining the protrusion/recess-shaped state. In this case, when a predetermined gap G is provided between the adjacent gears, it is possible to bring the sheet into intimate contact with the peripheral surface of the first roll, without exerting any excessive stretching force or cutting effect due to the protrusion/recess engagement of the rolls on the sheet. The size of the gap G is preferably in the range of 0.1 to 50 mm, and more preferably, of approximately 0.1 to 5 mm.

FIG. 6-5 is an enlarged perspective view of a main portion of a first roll 51 according to another embodiment (51B). In the first roll of this embodiment, a plurality of gears 61c and second gears 61d constitutes as spur gears are combined, and the gears are coaxially mounted on a rotation shaft 65 in a roll-like configuration. All the gears have the same tooth width. Each gear is open at the center, and the rotation shaft 65 is inserted into the opening. The gears and the rotation shaft 65 have cutout portions (not shown), into which a key (not shown) is inserted, whereby idling of the gears is prevented.

The diameter of a circle at the tooth tip of the second gears 61d is smaller than the diameter of a circle at the tooth tip of the first gears 61c. More specifically, it is preferable that the diameter of a circle at the tooth tip of the second gears (spacers) is smaller by 0.5 to 10 mm than the diameter of a circle at the tooth tip of the first gears.

In the first roll 51B of this embodiment, a first gear 61c is disposed on either side of a second gear 61d, and a plurality of gear groups 66, each of which has the above-mentioned three gears, are deployed. In the gear groups 66, the first gears 61c and the second gears 61d are arranged such that the teeth of the gears are arranged in parallel in the roll rotation axial direction. As a result, in each gear group 66, protrusions 67 and recesses 68 are formed alternately along the rotating direction of the roll. Each of the protrusions 67 has either the teeth of three gears (i.e., two first gears 61c and one second gear 61d) arranged in parallel in the roll rotation axial direction (indicated at 67a in the drawing), or the teeth of two first gears 61c arranged in parallel in the roll rotation axial direction (indicated at 67b in the drawing).

Two or more gear groups 66 are used. The gear groups 66 are arranged such that the pitches of the protrusions and recesses of the adjacent gear groups 66, 66 differ from each other. In this embodiment, the protrusions and recesses of the adjacent gear groups 66, 66 are offset by 0.5 pitch.

In each gear group 66, between two first gears 61c, a plurality of gap portions 69 are formed at fixed intervals along the direction in which the roll 51B rotates. Each gap portion 69 is formed by two first gears 61c and a second gear 61d situated therebetween. More specifically, each gap portion 69 is defined by the opposing side surfaces of the two first gears 61c and two adjacent teeth of the second gear 61d. Thus, the number of gap portions 69 formed is the same as the number of teeth of the second gear 61d. The gap portions 69 are opened to the exterior.

The first gear 61c has a plurality of openings 60 arranged so as to surround the opening at the center through which the rotation shaft 65 is inserted. The openings 60 are of the same diameter, and are formed at equal distances from the center of the gear. The angles formed by adjacent openings 60, 60 and the gear center are the same. The number of openings 60 in each gear 61c is the same as the number of teeth of the second gear 61d. Further, when assembling the gear groups 66, the first and second gears 61c, 61d are arranged such that the openings 60 are situated between adjacent teeth of the second gear 61d. In the state in which the gear groups 66 are thus assembled and arranged such that the pitches of the protrusions and recesses of the gear groups 66 differ from each other, the openings 60 of the first gears 61c are continuous in the rotation axial direction of the roll 51B, and there are formed within the roll a plurality of suction paths 61 extending in the rotation axial direction. The suction paths 61 communicate with the above-mentioned gap portions 69.

At least one end of the suction paths 61 leads to a suction source such as a blower or a vacuum pump (not shown). Thus, when the suction source is operated to perform sucking operation, the air is sucked in from the gap portions 69 through the suction paths 61.

Figure 7:
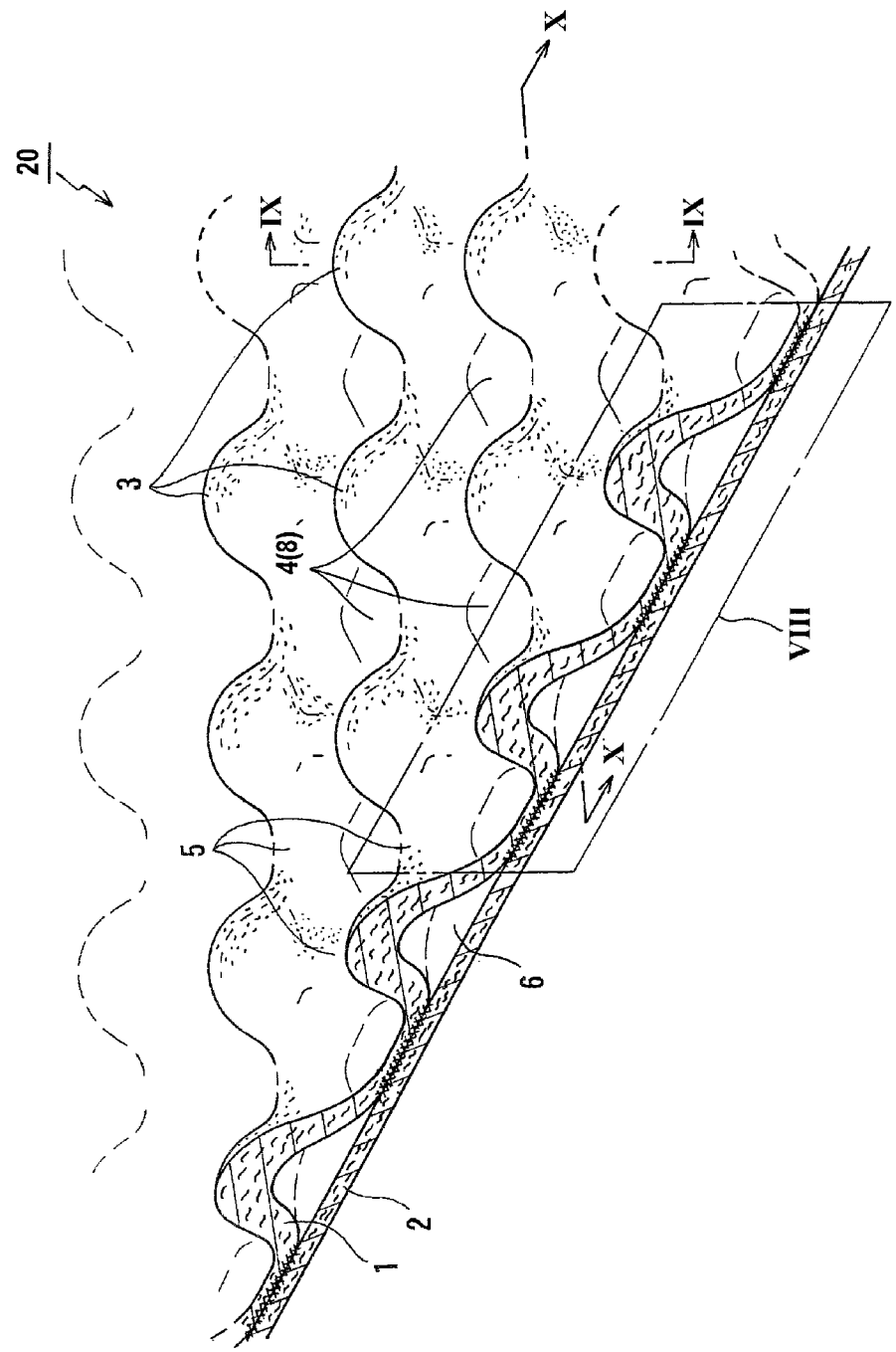
FIG. 7 is a schematic perspective view, partially in section, of a topsheet in a shaped sheet according to another embodiment (Second Embodiment) of the present invention.
Figure 8:
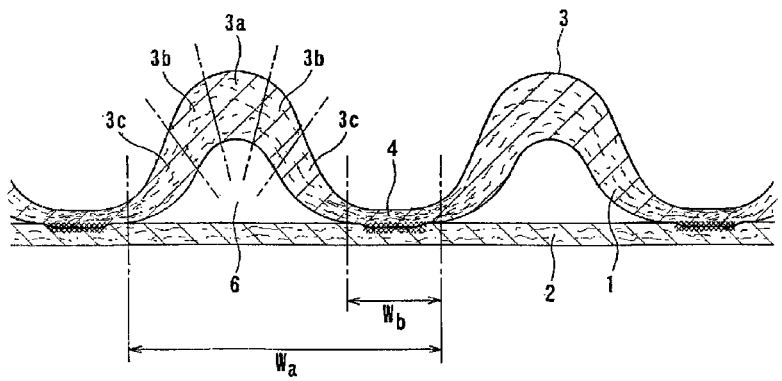
FIG. 8 is an enlarged sectional view of a region VIII of the shaped sheet illustrated in FIG. 7.
Figure 9:
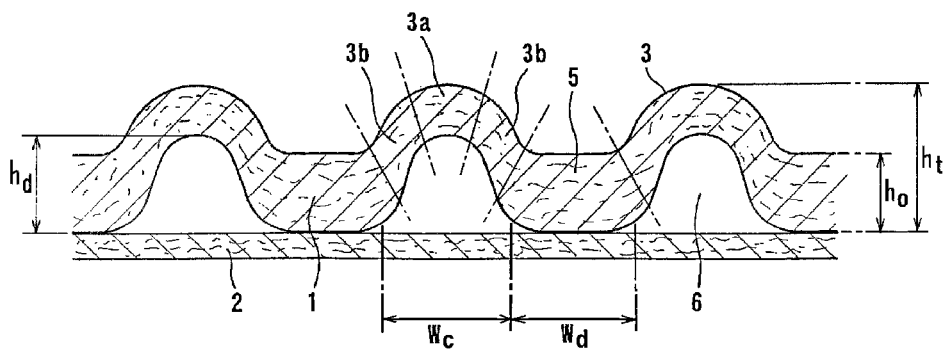
FIG. 9 is an enlarged sectional view, taken along the line IX-IX, of the shaped sheet illustrated in FIG. 7.

FIG. 7 is a partially-cutaway schematic perspective view of a topsheet 20 according to another embodiment (Second Embodiment) of the shaped sheet of the present invention. FIG. 8 is an enlarged sectional view of a region VIII of the shaped sheet of FIG. 7. FIG. 9 is an enlarged sectional view of the shaped sheet of FIG. 7 taken along the line IX-IX. In the topsheet 20 of the Second Embodiment, the structure portions, dimensional lines, and the like, functionally common to the above-mentioned topsheet 10 of the First Embodiment, are indicated by the same reference symbols.

In the topsheet 20 of the Second Embodiment, each of the protrusions 3 arranged in a staggered manner has the connecting portions 5 for being barriers on all four sides, and adjacent protrusions 3 are connected with each other by the connecting portions 5 for being barriers on the four sides. The connecting portions 5 for being barriers on the four sides are arranged so as to substantially divide each protrusion 3 into four equal parts in the sheet surface direction, that is, at positions of approximately 45 degrees around the protrusion 3 that is to be the center. In this way, on the upper layer sheet 1 side (the skin side) of the topsheet 20, there is formed a distinctive mountain-chain-like mesh surface configuration in which a plurality of mountains (protrusions) are connected by ridges on the four sides. Here, while the upper layer sheet 1 and the lower layer sheet 2 are bonded together intermittently by embosses formed at the recesses 4, it is also possible to form the topsheet solely by the upper layer sheet 1 shaped into protrusion/recess configuration as mentioned in the above.

In the Second Embodiment, the protrusions 3 are portions shaped so as to protrude to the skin side surface provided on the upper layer sheet 1. In the sectional view of FIG. 8, each protrusion 3 is formed so as to be situated between two recesses 4 (see FIG. 8). Further, each protrusion 3 is functionally divided into the apex portion 3*a*, the shoulder portion (edge) 3*b*, and the side portion 3*c*. In particular, it exhibits a substantially mound-shaped configuration rounded from the apex portion 3*a* toward the shoulder portion 3*b*. On the other hand, in the sectional view of FIG. 9, the adjacent protrusions are connected by the connecting portions 5 for being barriers. Here, while each protrusion 3 has the apex portion 3*a* and the shoulder portion 3*b*, in this sectional view, the side portion 3*c* is not distinguished from the connecting portion 5 for being barrier but integrated and continuous therewith. Further, the interiors of the connecting portions 5 for being barriers are filled with fibers. While in this embodiment the upper layer sheet 1 and the lower layer sheet 2 are not bonded together in the regions of the connecting portions 5 for being barriers, it is preferable that the two sheets are functionally in contact with each other. However, the two sheets may be in a non-contact state over some interval insofar as the function of the connecting portions 5 for being barriers is maintained. As in the sectional view of FIG. 9, also in the section taken along the line X-X in FIG. 7 (a sectional diagram of which is not shown), the protrusions 3 are connected via the connecting portions 5 for being barriers.

In the topsheet 20 of the Second Embodiment, the dimensions of the width $w_a$ and the width $w_b$ and the preferable range of their ratio ($w_b/w_a$) are the same as those of the First Embodiment described above. However, in the Second Embodiment, the width $w_c$ of the protrusions in the sectional view of FIG. 9 is preferably in the range of 2 to 4 mm, and the width $w_d$ of the connecting portions is preferably in the range of 0.5 to 2 mm. The distance $h_d$ of the widest portion of the dome-shaped space 6 in the protrusion, the height $h_t$ of the protrusion 3, the height $h_o$ of the connecting portion 5 for being barrier, and the ratio of the height of the connecting portion 5 for being barrier to the height of the protrusion 3 ($h_o/h_t$) are the same as those of the First Embodiment. Further, the preferable ranges of the density $D_t$ of the apex portion 3*a* of the protrusion, the density $D_o$ of the connecting portion 5 for being barrier, and the fiber density $D_b$ of the recess are the same as those of the First Embodiment described above.

The topsheet 20 of the Second Embodiment has the distinctive outer surface configuration and the inner surface configuration of the sheet as described above, making it possible to prevent spread of urine, loose feces or the like in the surface direction. Further, due to the interaction of the fiber density gradients of the protrusions 3, the connecting portions 5 for being barriers, and the recesses 4, it is possible to realize a dry feel for the skin. Further, due to the spatial network formed by the distinctive sheet inner space and the outer surface configuration, loose feces or the like can be dealt with in an excellent manner and superb drape characteristics can be imparted. These effects are the same as those of the First Embodiment described above.

A distinctive effect of the Second Embodiment is that, due to the arrangement of the connecting portions 5 for being barriers on the four sides of each protrusion 3, it is possible to exert the diffusion preventing function for loose feces or excrete liquid such as urine on all the four sides of each protrusion 3. Further, since the inner spaces 6 are independent from one another, it is possible to suppress still more effectively spread in the surface direction of loose feces or the like once retained inside. Thus, for example, when loose feces or the like is to be retained as much as possible at a single location and spread thereof in the surface direction is to be strictly suppressed, it is preferable to apply the topsheet of the Second Embodiment to the absorbent article.

Figure 10:
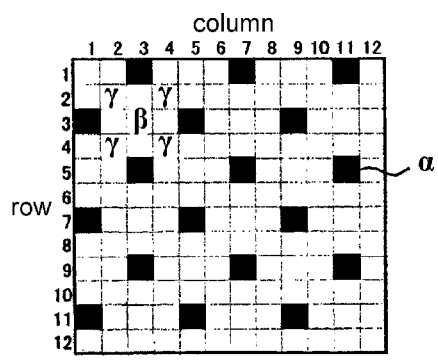
FIG. 10 is a pattern chart that depicts a four-point embossing pattern in a coordinate system.

The topsheet 20 of the Second Embodiment can be manufactured in the same manner as the topsheet 10 of the First Embodiment described above. For example, it can be manufactured by the process as illustrated in FIG. 6-1. Thus, the teeth 51*a* of the roll 51 forming the recesses 4 are arranged, for example, in a four-point seal pattern as illustrated in FIG. 10, in which four embosses a form one pattern element. Then, each tooth 52*a* of the roll 52 is arranged so as to be at the central position β of the above-mentioned pattern element including four points, and the protrusion 3 is shaped from within the space 6. In this way, shaping is performed by engaging the teeth 51*a* and 52*a* with each other, thereby obtaining a topsheet 20 shaped in a four-point sealing pattern, in which the connecting portions 5 for being barriers are situated at positions γ. While FIG. 10 only illustrates the position β for the protrusion 3 (protrusion apex 3*a*) and the positions γ for the connecting portions 5 for being barriers, with respect to the first element formed by the four embosses (1, 3), (3, 1), (3, 5), and (5, 3), in this embodiment, the structure of the protrusions 3, the connecting portions 5, and the recesses 4 respectively at the positions α, β, and γ are expansively repeated in the surface direction also for other emboss elements.

Figure 11:
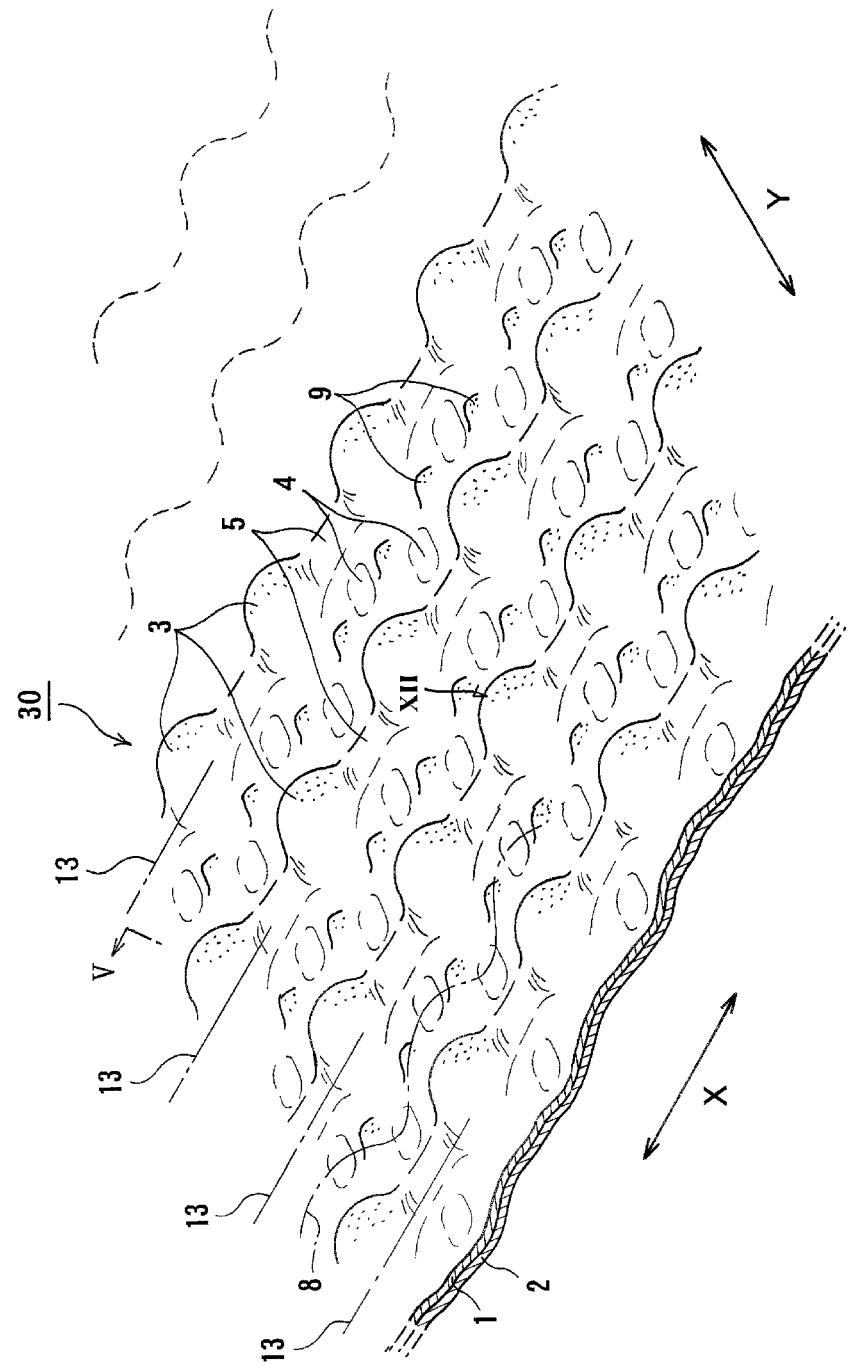
FIG. 11 is a schematic perspective view, partially in section, of a main portion of a topsheet according to an embodiment (Third Embodiment) of the present invention.
Figure 12:
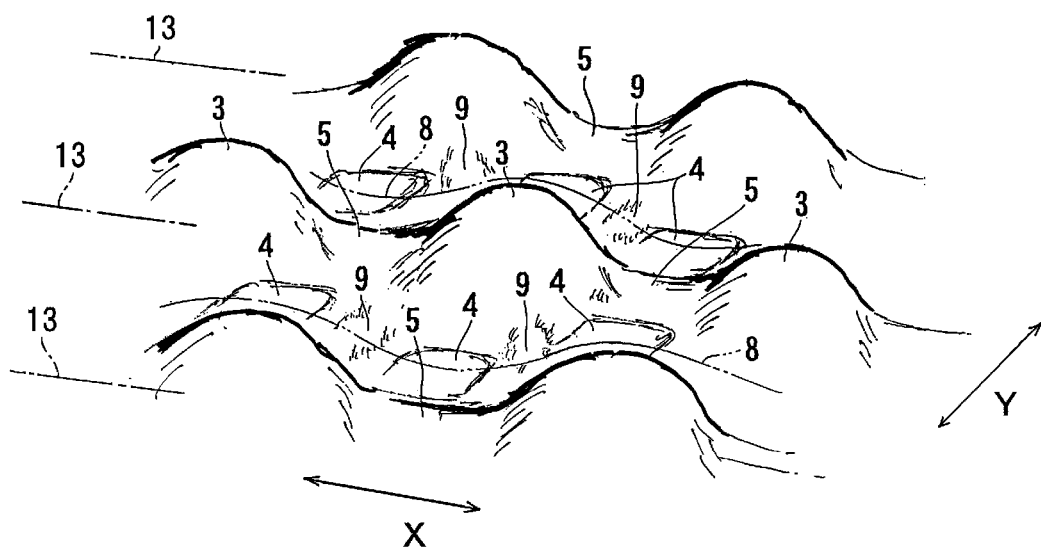
FIG. 12 is an enlarged perspective view of a region XII and the vicinity thereof of FIG. 11.

FIG. 11 is a schematic partial perspective view of the main portion of a topsheet for an absorbent article according to an embodiment (Third Embodiment) of the present invention, and FIG. 12 is an enlarged perspective view of the region XII of FIG. 11 as seen from a somewhat different angle. A plurality of protrusions 3 are provided in a staggered manner on the upper layer sheet 1 side of a topsheet 30 for an absorbent article according to the Third Embodiment, that is, on the side to be brought into contact with the skin of the wearer. The protrusions 3 contain, in their insides, the dome-shaped spaces 6 formed by shaping of the upper layer sheet 1 in a protrusion/recess configuration.

The protrusions 3 are connected by the connecting portions 5 for being barriers to form the protrusion rows 13. The dome-shaped spaces 6 in the protrusions are connected by the tunnel-like spaces 7, and recesses are arranged on both sides of the connecting portions 5 for being barriers of the protrusion rows (In the Third Embodiment, the connecting portions 5 for being barriers may, in particular, be referred to as the "ridge portions"). This sheet configuration is the same as that of the First Embodiment, and the drape characteristics, the satisfactory fitting property, and the cushion property, and the function by which liquid or the like is transferred to the absorbent member to be concealed therein, each of which is exhibited owing to the sheet configuration, are the same as those of the First Embodiment.

The spaces 6 inside the dome-shaped protrusions 3 are spatially continuous with one another via the tunnel-like spaces 7, whereby loose feces or the like is effectively concealed in the inner space network. This function, which is the same as that of the First Embodiment, will be described in detail here.

When loose feces or the like is excreted, it is first transferred toward the bottoms of the groove portions 8 in the outer surface of the topsheet and stays there. After this, or simultaneously with this, the loose feces or the like passes between the fibers of the topsheet, and is retained within the inner spaces 6. Here, the loose feces or the like accommodated in the inner spaces 6 is gradually deprived of water by the absorbent member or the like arranged underneath the topsheet, and is gradually dried to attain a state in which it is free from backward flow, thus maintaining a satisfactory feel for the wearer. Further, in the topsheet of this embodiment, the inner spaces 6 of the dome-shaped protrusions are connected together by the tunnel-like spaces 7. Thus, when, for example, a large body pressure is applied to the topsheet, it is possible to suppress and prevent backward flow toward the skin-contact surface side owing to suppression of deformation by the ridge portions and the like. Further, the loose feces or the like accommodated in the spaces 6 is diffused in the surface direction of the topsheet via the tunnel-like spaces 7, thereby suppressing and preventing backward flow to the skin-contact surface side. As a result, even when loose feces or highly viscous liquid or semi-solid substance contained in vaginal discharge is excreted, it is possible to maintain for a long period of time extremely satisfactory wearing comfort and a clean skin condition. Taking into consideration the function as described above, the distance $h_n$ (FIG. 2) of the widest portion of the tunnel-like spaces 7 inside the ridge portions is preferably in the range of 0.1 to 5 mm and, more preferably, of 0.1 mm to 1 mm.

Unlike in the First Embodiment where there are second connecting portions 12, in the topsheet 30 of the Third Embodiment, there are no second connecting portions (12) but are arranged small protrusions 9 at the corresponding positions. The small protrusions 9 do not connect the protrusions 3 to one another, and are arranged in the groove portions 8 as protrusions independent of the protrusions 3. In the Third Embodiment, the small protrusions 9 are lower than the connecting portions 5 for being barriers, and the ratio of the height $h_r$ of the small protrusions 9 to the height $h_o$ of the connecting portion 5 for being barrier (ridge portions), ($h_r/h_o$), is preferably in the range of 0.1 to 0.9. In the Third Embodiment, the small protrusions 9 are higher than the bottom portions of the recesses 4 (the lowermost portions on the non-skin-contact side). Due to the small protrusions 9, the bottom surfaces of the groove portions 8 are not flat U-shaped grooves but the functional bumpy (asperity) surface as described above. Further, while on the upper layer sheet back surface side the small protrusions 9 are in contact with the lower layer sheet 2, they are not emboss-bonded like the recesses 4. In this way, the ridge portions 5 and the small protrusions 9 differing in height, width, and bonding state are arranged, among the protrusions 3 and the troughs 4 arranged in a staggered manner, whereby it is possible to attain a function such as drape characteristics which cannot be obtained by simply forming groove-like portions by linear seals.

When spaces are simply formed within the protrusions, the protrusions are likely to be crushed when a large pressure is applied thereto. In the topsheet of this embodiment, however, the protrusions 3 are connected by the thin and narrow connecting portions for being barriers (ridge portions) 5 into a mountain-chain-like configuration, so it is possible to prevent excessive deformation when the protrusions 3 are strongly pressed while maintaining a satisfactory cushion property. As a result, the protrusions are not crushed to an excessive degree, and it is possible to realize a satisfactory cushion property. The connecting portions for being barriers (ridge portions) 5 and the small protrusion 9 are present between the recesses 4 formed by joining or bonding the upper layer sheet and the lower layer sheet, and their curvature is smaller than that of the protrusions 3, so they are little subject to deformation. Thus, it is possible to suppress deformation stepwise through the respective heights of the ridge portions 5 and the small protrusions 9 with respect to deformation of the protrusions 3. Thus, when a small pressure is applied, the apex portions of the protrusions 3 and the periphery thereof are deformed to a slight degree to provide a soft feel, and, when a large pressure is applied, not only the protrusions 3 but also the connecting portions for being barriers (ridge portions) 5 and the small protrusions 9 exert an elastic support function. As a result, even when various levels of pressure are applied to the topsheet 30 due to the movement and weight of the wearer, the topsheet functionally responds thereto to exhibit an appropriate repulsive force, thus providing a soft and gentle feel to the skin.

Further, the protrusions 3 are not isolated but are connected by the connecting portions for being barriers (ridge portions) 5, so, even when the sheet is bent, the protrusions 3 are not easily deformed in an irreversible fashion. As a result, even when the sheet is subjected to large bucking or bending deformation due to the undulation of the skin or vigorous movement, once released, the connection structure of the protrusions 3 and the ridge portions 5 is restored, and the sheet is restored to the original soft state with sufficient thickness. Further, because the deformation of the protrusions 3 is suppressed to an appropriate height as described above, the viscous liquid or the like accommodated in the spaces 6 is not easily squeezed out, and backward flow thereof toward the skin-contact surface side is suppressed, thereby maintaining a dry and clean wearing state. The effects due to the interactions of the protrusions 3, the connecting portions for being barriers (ridge portions) 5, and the small protrusions 9 of the Third Embodiment, can also be exerted similarly insofar as that the protrusions 3, the first connecting portions 11, and the second connecting portions in the First Embodiment correspond to the above-mentioned components, respectively.

Figure 13:
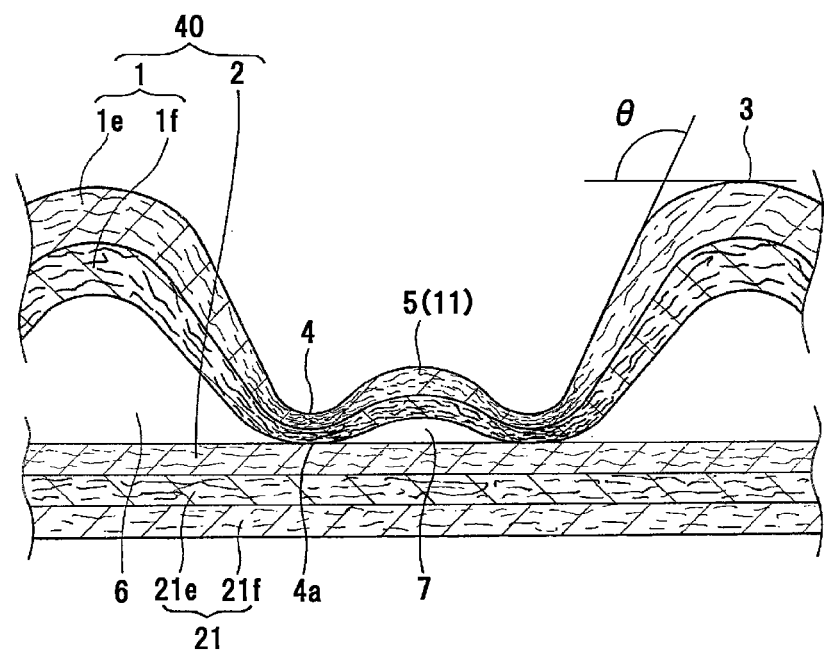
FIG. 13 is a sectional view showing by enlarging a main portion section of a topsheet in a shaped sheet according to still another embodiment (Fourth Embodiment) of the present invention.

FIG. 13 is an enlarged sectional view of a main portion of a shaped sheet according to still another embodiment (Fourth Embodiment) of the present invention. The main portion section illustrated in FIG. 13 corresponds to the section illustrated in FIG. 3 in relation to the First Embodiment. It illustrates the first connecting portion 11, with its central portion further enlarged. However, their sectional configurations differ from each other in the way they are schematically depicted.

The upper layer sheet 1 of the Fourth Embodiment includes a first layer 1e on the skin-contact surface side and a second layer 1f on the non-skin-contact surface side. The fibers forming the first layer are thinner than the fibers forming the second layer. While the specific fiber diameter of each layer may be determined as appropriate, the fineness ($E_{1d}$) of the fibers of the first layer is preferably in the range of 1.0 to 4.4 dtex, and more preferably, of 1.2 to 3.3 dtex. The ratio of the fineness ($E_{1d}$) of the fibers used in the first layer to the fineness ($E_{2d}$) of the fibers used in the second layer, ($E_{1d}/E_{2d}$), is preferably in the range of 10 to 70% and, more preferably, of 20 to 60%.

The fineness ($E_{2d}$) of the fibers forming the second layer 1f of the upper layer sheet is preferably in the range of 2.2 to 7.8 dtex, and more preferably, of 3.3 to 5.6 dtex. The fineness ($E_{3d}$) of the fibers forming the lower layer sheet 2 is preferably in the range of 1.0 to 4.4 dtex and, more preferably, of 1.2 to 3.3 dtex. While there are no particular limitations regarding the ratio of the fineness ($E_{2d}$) of the fibers forming the second layer 1f of the upper layer sheet to the fineness ($E_{3d}$) of the fibers forming the lower layer sheet 2, ($E_{2d}/E_{3d}$), the ratio is preferably in the range of 150% to 800% and, more preferably, of 150% to 500%.

As in the First Embodiment described above, in the Fourth Embodiment, the topsheet 40 is shaped so as to exhibit the protrusions 3, the connecting portions 5 for being barriers (first connecting portions 11 and second connecting portions 12), and the recesses 4. It is also possible, as in the Third Embodiment, to shape the sheet so as to form the small protrusions 9 instead of the second connecting portions 12.

In this embodiment, the protrusions 3 have a round, substantially mound-shaped sectional configuration. More specifically, the side portions of the protrusions are formed not as vertical walls orthogonal to the lower layer sheet 2 but as gently-sloped surfaces as illustrated in the drawing. The shoulder portion 3b (see FIG. 3) of each protrusion is rounded. More specifically, while there are no particular limitations regarding the edge angle θ (see FIG. 13), the angle is preferably in the range of 95 to 140 degrees and, more preferably, of 100 to 130 degrees. In the present invention, the edge angle θ is defined and measured as an angle made by a straight line (i) obtained by cutting the protrusion 4 with a razor edge from the apex of the protrusion 4 in a direction parallel to the X-direction and extending from the apex parallel to the sheet surface direction, and by a straight line (ii) extending from the side portion 3c. By thus forming a rounded edge (shoulder portion), no discomfort is caused if the absorbent article is moved out of position due to movement or the like of the wearer, which is preferable.

Further, by forming the side portion 3c as a slope (i.e., by making the angle θ large), it is possible to reduce the area of the apex portion 3a of the protrusion (see FIG. 3). By thus reducing the area of the apex portion 3a of the protrusion, which comes into direct contact with the skin of the wearer, it is possible to reduce the contact area with the wearer. As a result, it is possible to prevent the sheet which has once absorbed liquid from coming into surface contact to cause the wearer to experience stickiness and, due to appropriate point contact, it is possible to provide a satisfactory cushion property and a dry feel to the touch. Further, when the absorbent article is moved out of position, the discomfort caused by rubbing of the topsheet is reduced, thus providing an article excellent in feel to the touch and wearing feel.

In the Fourth Embodiment, the upper layer sheet is formed in a two-layer structure, and the fineness of each sheet is set to a specific level, so it is possible to obtain a desired protrusion configuration in a more stable manner. The function of this stability in shaping is as follows: in the Fourth Embodiment, when forming the protrusion containing a hollow space, the upper layer sheet is formed in two layers, and a rigidity gradient is generated in the sheet, so the sheet can be expected to be shaped into a desired configuration more easily. Further, when shaping the protrusions 3 using gears generating suction force, the way the sheet surface is held in intimate contact due to this suction is varied due to the gradient in the diameter of in-sheet fibers, so the bumpy configuration thus-obtained is easily stabilized to a desired one.

In the Fourth Embodiment, the upper layer sheet 1 and the lower layer sheet 2 may be formed of the same kind of fiber material or different kinds of fiber materials. It is preferable that each sheet is formed of a sheet material substantially free from stretching and contraction. In this regard, each sheet may be substantially free from stretching and contraction in the MD and CD directions, or it may be expanded and contracted in only one of the MD and CD directions. In the case of a non-woven fabric having stretchability solely in one direction, it is preferable that the sheets are overlaid such that the stretching/contracting directions of the two sheets coincide with each other. By using such a sheet material, in performing shaping by a suction gear and a roll thereof as described below, it is possible to effect shaping into a desired configuration, in a stable manner, and with satisfactory reproducibility.

Further, as in the Fourth Embodiment, by making the fibers of the outer first layer 1e of the upper layer sheet 1 constituting the protrusions thinner than the fibers of the inner second layer 1f, it is possible to make the protrusions little subject to crushing, and to maintain a satisfactory feel to the touch and a cushion feel during wearing. It is presumed that this can be realized since the fibers of the inner second layer 1f forming the protrusions are thicker, so that, in particular, the side portions of the protrusions do not easily collapse during compression. In other words, the second layer 1f of the protrusion inner side serves to support the protrusions 3 as a whole like a pier, making the protrusions relatively free from crushing. On the other hand, the apex portions of the protrusions can be deformed with an appropriate elastic force, making it possible to attain a high-quality cushion property as if bulky cotton is placed on a cylindrical wall portion of high rigidity. When no compression is being effected, the restoring force due to the larger thickness of the fibers of the second layer is exerted, and, synergistically with the supporting function like a pier as described above, the rigidity in the layer is made effective, and the original configuration is easily restored after the protrusions have been compressed. In this way, during compression, the protrusions 3 are elastically deformed while maintaining a predetermined height, and are quickly restored to the original configuration when no compression is effected.

Further, in the Fourth Embodiment, the fibers of the outer first layer 1e of the upper layer sheet forming the protrusions is thinner than the fibers of the inner second layer 1f, whereby it is possible to exert an excellent function in terms of absorption of liquid or the like. This will be described more specifically. As explained above, the fibers of the second layer are thicker than the fibers of the first layer, so the fiber interval of the second layer generally expands to a larger degree than the fiber interval of the first layer. As a result, there is formed on the second layer side a space where the fibers are sparse, so, for example, loose feces containing a large amount of liquid is drawn in and strongly collected. In particular, the solid portion of loose feces is drawn into the inner spaces 6 of the protrusions 3 to be concealed therein, so it is possible to suppress the discomfort caused when loose feces comes into direct contact with the skin of the wearer.

Further, around the bonding points 4a of the recesses, the fibers of the first layer 1e and the second layer 1f forming the upper layer sheet 1 are compressed while being somewhat elongated. Thus, around the bonding points 4a, there is generated a function to strongly draw in liquid by a large capillary force. As a result, in the case of loose feces containing a large amount of liquid, the liquid is concentrated around the recesses 4, and this liquid portion is quickly sent to the absorbent member through the lower layer sheet 2. In this instance, as in the Fourth Embodiment, a sublayer 21 is arranged between the topsheet 1 and the absorbent member (not shown in FIG. 13), whereby the liquid feeding function is further enhanced, which is preferable.

As stated above, the diameter of the fibers of the inner second layer 1f of the upper layer sheet 1 forming the protrusions is large, and the inter-fiber interval is generally large, so, even in the case of semi-solid loose feces, it is effectively collected in the hollow spaces. In this instance, the fiber diameter of the fibers forming the lower layer sheet 2 is made smaller than the fiber diameter of the second layer 1f of the upper layer sheet, making it approximately the same as, for example, the fiber diameter of the first layer 1e. Then, three-dimensional shaping is not effected on the lower layer sheet 2, so the inter-fiber interval is not enlarged, and loose feces does not easily enter the absorbent member through the lower layer sheet 2. In this way, the solid portion of loose feces is effectively trapped in the spaces 6 while making it possible to quickly take solely the liquid portion into the absorbent member. That is, even in the case of loose feces containing a large amount of liquid, it is possible to retain the solid portion in the spaces 6, and to prevent soiling of the absorbent member, deteriorating the absorbing function, and the like to an excessive degree. On the other hand, it is possible to selectively transfer solely the liquid portion to the absorbent member, providing an extremely satisfactory, clean and dry wearing feel for the wearer.

That is, as stated above, the fibers forming the topsheet are specific to each layer. The inter-fiber interval of the second layer is preferably made larger than the inter-fiber interval of the first layer, and, more preferably, the inter-fiber interval of the first layer is made larger than the inter-fiber interval of the lower layer, whereby it is possible to provide high treatment function for, in particular, loose feces containing a large amount of liquid. In the present invention, unless otherwise specified, the "inter-fiber distance" is an average inter-fiber distance in a predetermined region of the sheet. The inter-fiber distance is calculated from the thickness and weight of the non-woven fabric, and the fiber construction of the constituent web, and it is defined by the following formula.

[Mathematical Formula 1]

$$\text{Average inter-fiber distance} = \sqrt{\frac{td}{9000w}} \quad \text{Formula (1)}$$

In formula (1), t is the thickness [mm] of the non-woven fabric, w is the weight [g/m$^2$] of the non-woven fabric, and d is the fineness [denier] of the fibers constituting the fiber web. In the present invention, the inter-fiber distance is preferably in the range of 70 to 100 μm in the first layer for the upper layer sheet, and in the range of 120 to 160 μm in the second layer. The inter-fiber distance is preferably in the range of 70 μm to 90 μm in the lower layer sheet.

In the Fourth Embodiment, when using a stretchable non-woven fabric, the stretching ratio in the stretching direction is preferably in the range of 105 to 200% and, more preferably, of 105 to 120%. Herein, the term "stretchability" means that, when a stretching ratio is, for example, 105%, stretching in excess of a stretch ratio of 5% with respect to the length in the material stretching direction leads to material rupture or causes permanent distortion. Furthermore, the term "substantially non-stretchable non-woven fabric" means one having a stretching ratio of 105% or less, causing material rupture or permanent distortion upon being stretched at a stretch ratio in excess of 5%. Here, when the material is stretched or expanded to twofold its original length, the stretching ratio is 200%. Further, when the material increases to twofold its original length, the stretch ratio is 100%.

As the non-woven fabric, use may be made of an ordinary one. Examples of the non-woven fabric include various non-woven fabrics manufactured by the card method, such as thermal bond non-woven fabric, spun bond non-woven fabric, melt blown non-woven fabric, spunlace non-woven fabric, and needle punch non-woven fabric. When bonding the upper layer sheet 1 and the lower layer sheet 2 together by fusion-bonding as described below, it is preferable that the non-woven fabric contains fusion-bonding fibers. As the fusion-bonding fiber, it is preferable to adopt one of sheath/core structure, such as PET/PE or PP/PE. Further, it is preferable to perform hydrophilic treatment on the non-woven fabric using surface active agent or the like. Of the constituent fibers of the upper layer sheet 1 and the lower layer sheet 2, a combination of PET/PP fibers is preferable.

In the upper layer sheet 1 of the topsheet 40 of the Fourth Embodiment, it is preferable that the basis weight of the outer first layer 1e is less than or equal to that of the inner second layer 1f. Regarding the thickness, it is preferable that the thickness of the first layer is less than or equal to the thickness of the second layer. Further, it is preferable that the basis weight of the upper layer sheet 1 is more than or equal to that of the lower layer sheet 2. Regarding the thickness, it is preferable that the thickness of the upper layer sheet 1 is larger than or equal to that of the lower layer sheet 2. Regarding the fineness of the fibers forming the upper layer sheet 1 and the lower layer sheet 2, it is preferable that the fibers forming the second layer 1f of the upper layer sheet 1 are thicker than or of the same thickness as that of the fibers forming the lower layer sheet 2.

In the topsheet 40 of the Fourth Embodiment, the sublayer 21 is located in the lower portion thereof (See FIG. 13). It is preferable that the topsheet 40 and the sublayer 21 are bonded together, for example, intermittently, so no liquid is allowed to stay in the topsheet. In order that the absorbent member may easily draw in the liquid when the absorbent member is located beneath the sublayer 21, it is preferable that the bonding is conducted, for example, through sparse entire-surface bonding. The sublayer 21, which is located underneath the topsheet 40, is adapted to buffer the stress of any pressure applied from the skin side (topsheet side). As a result, the protrusions 3 of the three-dimensionally shaped topsheet are made less subject to crushing, making it possible to achieve a further improvement in terms of feel to the touch and cushioning feel.

Further, in the Fourth Embodiment, due to the presence of the sublayer 21, it is possible to enhance the absorption and diffusion of the liquid transferred from the topsheet 40. More specifically, it is effective to quickly draw in the liquid while suppressing liquid diffusion in the surface material, accelerating the liquid diffusion into the absorbent member. In this embodiment, the sublayer 21 includes two layers, i.e., a sublayer upper layer 21e and a sublayer lower layer 21f. The fibers forming the upper layer 21e of the sublayer 21 are thicker than the fibers forming the topsheet lower layer 21f to be located thereon. As a result, when, after concentrating the liquid on the recesses 4 of the upper layer and drawing it in to the lower layer sheet 2 side, the liquid is to be further transferred to the sublayer 21, it is possible to diffuse the liquid in the surface direction of the sublayer. This is due to the function that the fibers forming the sublayer upper layer 21e are thicker than those forming the lower layer 21f, so the density of the sublayer upper layer 21e is still lower, enhancing the diffusion force with respect to the liquid drawing-in force. In this way, when the liquid is further drawn into the sublayer lower layer 21f and the absorbent member, no saturation occurs with the liquid locally unevenly distributed, and the liquid can be absorbed and retained while spread in the surface direction. As a result, the liquid retaining amount and the absorption (drawing-in) speed of the absorbent article as a whole are enhanced.

As the material of the sublayer 21, it is preferable to use a non-woven fabric (examples of which include ones made of fibers formed of thermoplastic resin, such as polyolefin like polyethylene or polypropylene, polyester, and polyamide, and conjugate fibers formed of two or more of these resins), pulp, or curly cellulose stacked into a sheet form.

In the Fourth Embodiment, the fibers of the sublayer lower layer 21f are thinner than the fibers of the sublayer upper layer 21e. As a result, the density of the sublayer lower layer 21f is made higher than that of the sublayer upper layer 21e, and liquid once diffused into the sublayer upper layer 21e is quickly drawn into the sublayer lower layer 21f. In this way, the liquid received by the topsheet upper layer sheet 1 is first concentrated on the recesses 4 and, while doing so, the liquid is drawn into the lower layer sheet 2 through the periphery of the bonding interface 4a. Further, the liquid is transferred to the sublayer lower layer 21f while being diffused into the sublayer upper layer 21e. As a result, the liquid can be quickly sent to the entire absorbent member located beneath the sublayer. In this way, in this embodiment, due to the distinctive interaction of the functions of the individual layers of the topsheet and/or the individual layers of the sublayer, it is possible to quickly transfer the liquid to the absorbent member side without allowing it to stay on the skin-contact surface side of the topsheet.

The fineness ($E_{4d}$) of the fibers forming the sublayer upper layer 21e is preferably in the range of 3.3 to 15 dtex and, more preferably, of 5.6 to 10 dtex. While there are no particular limitations regarding the ratio of the fineness ($E_{3d}$) of the fibers forming the lower layer sheet 2 to the fineness ($E_{4d}$) of the fibers forming the sublayer upper layer 21e, ($E_{3d}/E_{4d}$), the ratio is preferably in the range of 0.15 to 0.8, and more preferably, of 0.2 to 0.5. The fineness ($E_{4d}$) of the fibers forming the sublayer lower layer 21f is preferably in the range of 2.0 to 5.6 dtex and, more preferably, of 2.2 to 4.4 dtex. While there are no particular limitations regarding the ratio of the fineness ($E_{4d}$) of the fibers forming the sublayer upper layer 21e to the fineness ($E_{5d}$) of the fibers forming the sublayer lower layer 21f, ($E_{4d}/E_{5d}$), the ratio is preferably in the range of 1.5 to 8, and more preferably, of 2 to 5.5.

There are no particular limitations regarding the method by which the sublayer upper layer 21e and the sublayer lower layer 21f are laminated and integrated. For example, the integration can be effected through hot-air treatment after overlaying the upper layer and the lower layer. The boundary between the sublayer upper layer 21e and the sublayer lower layer 21f is not a definite one, and it may have an inclined interface.

Figure 14:
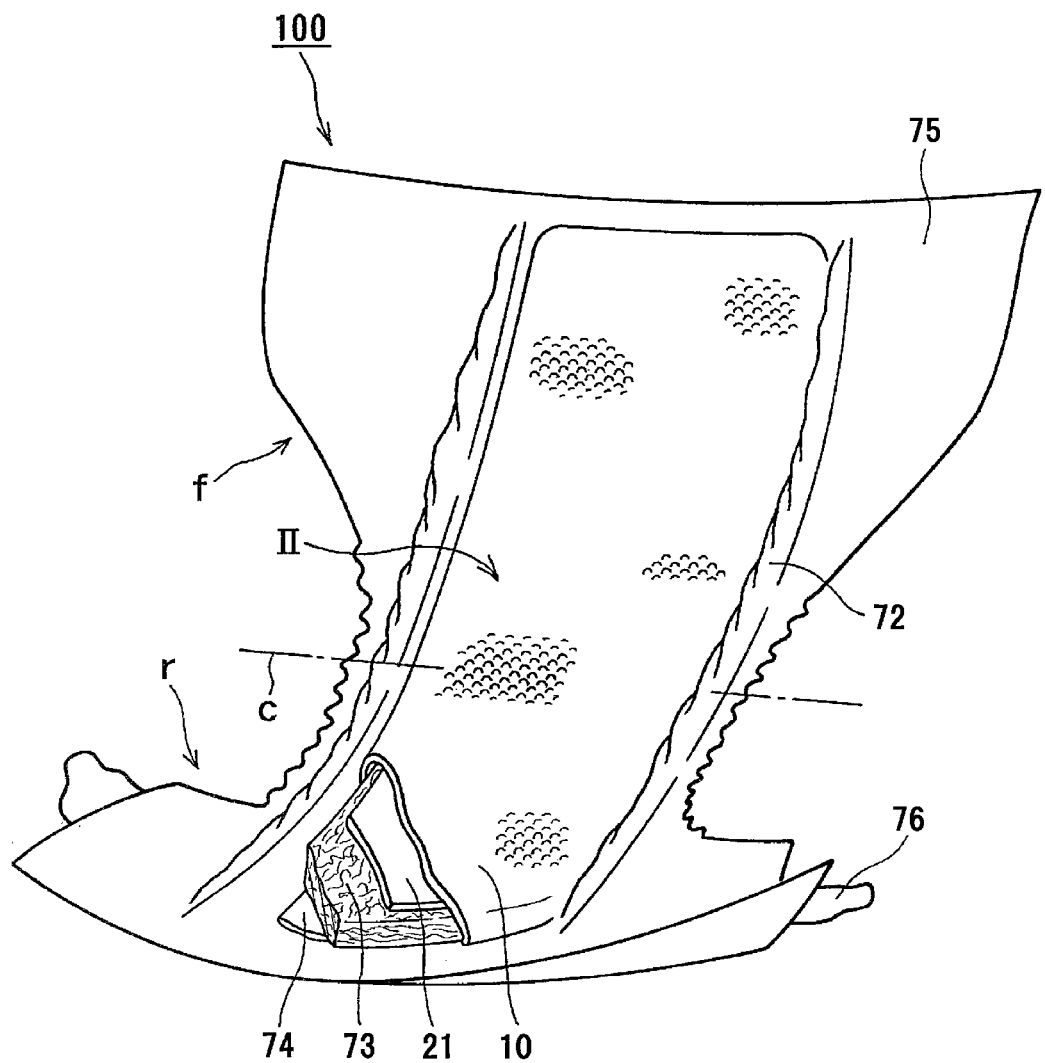
FIG. 14 is a partially cutaway schematic perspective view of a disposable diaper using a shaped sheet according to the present invention as the topsheet.

FIG. 14 is a partially-cutaway schematic perspective view of a disposable diaper to which the topsheet 10 of the First Embodiment is applied. The diaper illustrated in the drawing is a tape-type disposable diaper for infants. The diaper, as seen from the inner side (the skin-contact surface side), is developed in a plane and bent to some degree. It goes without saying that, instead of the topsheet 10 (First Embodiment), it is possible to apply the topsheet 20, 30, or 40 (Second, Third, or Fourth Embodiment) to the disposable diaper 100 of this embodiment.

The disposable diaper 100 of this embodiment has the liquid permeable topsheet 10 arranged on the skin-contact surface side, a liquid impermeable back sheet 75 arranged on the non-skin-contact surface side, and an absorbent member 73 provided between the two. It is preferable that the topsheet is located at the portion where the excretory liquid or the like, which is urine or feces, or menstrual blood or the like in the case of sanitary items, that is, at least near the excretory portion of the absorbent article.

In this embodiment, the sublayer 21 is provided between the topsheet 10 and the absorbent member 73. The back sheet 75 is in the developed state, with its both side edges being constricted at the central portion c in the longitudinal direction into a substantially sand-glass-like configuration, and it may have a single sheet or a plurality of sheets. In this embodiment, the back sheet 75 is provided with lateral leakage prevention gathers 72, whereby it is possible to effectively prevent lateral leakage of liquid or the like at the hip joint portion of the infant due to movement or the like. In the diaper of this embodiment, it is possible to further provide a functional structure portion, a sheet material, or the like. On the back sheet 75, there are arranged the topsheet 10 and the absorbent member 73, with the upper side of the absorbent member 73 being wrapped in the topsheet 10.

The diaper of this embodiment illustrated is of a tape type, and a fastening tape 73 is provided at a flap portion on the back side r. The tape 73 is attached to a tape attachment portion (not shown) provided on the flap portion on the abdomen side f, whereby it is possible to attach and fix the diaper in position. At this time, the central portion c of the diaper is gently bent inwards, with the absorbent member 73 extending from the hip portion to the lower abdomen of the infant, whereby the excretory substance can be properly absorbed and retained by the absorbent member 73.

The shaped sheet of the present invention is applicable to various uses.

In a preferred embodiment thereof, the shaped sheet of the present invention can be favorably used as the topsheet of an absorbent article or the like, exhibiting high absorption/retention property for liquid or the like. In particular, according to the shaped sheet of the present invention, it is possible to suppress or prevent excreted urine, loose feces or the like from being spread along the surface to leak. Further, according to the shaped sheet of the present invention, it is possible to suppress backward flow of excretory substances, such as feces, urine, sweat or the like, to adhere to the skin, thus protecting the skin of the wearer from rash or the like (skin irritation, eruption or inflammation of the skin).

Further, in a preferred embodiment thereof, the shaped sheet of the present invention exhibits such excellent effects of: having, along with the above-mentioned functions, flexibility and cushioning property; being soft to the touch; exhibiting a drape characteristic; and advantageously maintaining a satisfactory feel to the touch for a long period of time.

Further, in a preferred embodiment thereof, the shaped sheet of the present invention exhibits a satisfactory permeation treatment property, in particular, for high viscosity liquid. Further, according to the shaped sheet of the present invention, liquid backward flow does not easily occur even when the topsheet is crushed by body pressure applied thereto. Further, the shaped sheet of the present invention exhibits such excellent effects that, if once crushed, the sheet easily recovers its thickness, and, even after attachment, a soft and dry feel to the touch is advantageously maintained for a long period of time, providing a sheet of high air permeability in a direction parallel to the sheet surface.

The present invention will be described in more detail based on the following examples, but the invention should not be construed to be limited to those examples.

EXAMPLES

Example 1, Comparative Example 1

1. Preparation of a Test Sample of Diaper

Example 1

As the non-woven fabric forming the upper layer sheet, use was made of an air-through non-woven fabric of basis weight 18 g/m², formed by overlaying a sheath/core-type conjugate fiber in a size and weight of 2.2 dtex×51 mm and 6 g/m², and a sheath/core-type conjugate fiber in a size and weight of 4.4 dtex×51 mm and 12 g/m², each of whose core was composed of polyethylene terephthalate and each of whose sheath was composed of polyethylene. The upper layer was bent in the MD direction through shaping and was increased in weight, so, after the shaping, it would become 22 g/m² (The speed at which the upper layer was paid out was increased by approximately 20% as compared with the speed at which the lower layer sheet was paid out). As the non-woven fabric forming the lower layer sheet, use was made of an air-through non-woven fabric of basis weight 18 g/m² formed by a sheath/core-type conjugate fiber in a size of 2.2 dtex×51 mm whose core was composed of polyethylene terephthalate and whose sheath was composed of polyethylene. By using these sheets, a topsheet (test material 1) according to the First Embodiment was prepared, using the apparatus illustrated in FIG. 6-1. The thus-obtained topsheet (test material 1) had a distinctive sheet configuration as illustrated in FIGS. 1 to 4. The height $h_t$ of the protrusions was approximately 1.7 to 2.1 mm, and the height $h_o$ of the connecting portions for being barriers was approximately 0.6 to 1.0 mm. A predetermined sheet portion of the test material 1 was photographed in an enlarged state (magnification: 150-fold) by an optical microscope (Digital HF Microscope VH-8000 (trade name), manufactured by Keyence Corporation). The ratio of the fiber density of the protrusions to that of the connecting portions for being barriers, $(D_t/D_o)$, of the test material 1 as obtained by this microscopic image was approximately 0.5.

An absorbent member 1 was prepared, which had: an absorbent core of 100×150 mm wrapped in a tissue (formed by pulp in an amount of 200 g/m² and an absorbent polymer in an amount of 280 g/m²); a sublayer on the absorbent core (air-through non-woven fabric of 40 g/m²); and the topsheet (test material 1) thereon. The thus-obtained absorbent member 1 of 100×150 mm was placed on a moisture permeable sheet having an outer layer sheet of 100×330 mm (composite sheet of a non-woven fabric and a moisture permeable sheet), thus preparing a diaper test sample 1. In the diaper test sample 1, so that the pulp and absorbent polymer of the absorbent member and artificial urine poured in would not leak, the surface of the absorbent member 1 of the periphery of the absorbent member 1 was sealed by an outer layer sheet so as to cover it by approximately 10 mm.

Comparative Example 1

Use was made of an air-through non-woven fabric, formed by overlaying: as the fiber web forming the upper layer sheet, a basis weight of 10 g/m² of a sheath/core-type conjugate fiber in a size of 2.0 dtex×51 mm whose core was composed of polyethylene terephthalate and whose sheath was composed of polyethylene; and, as the fiber web forming the lower layer sheet, a basis weight of 15 g/m² of a mixture of a sheath/core-type conjugate fiber in a size of 5.6 dtex×51 mm whose core was composed of polyethylene terephthalate and whose sheath was composed of polyethylene, and a sheath/core-type conjugate fiber in a size of 5.6 dtex×51 mm whose core was composed of polypropylene and whose sheath was composed of polyethylene, in which the mixture contained the two conjugate fibers in equal amounts. These sheets were overlaid and bonded together, thereby obtaining a topsheet (test material c1) for comparison. The thickness of the topsheet (test material c1) was approximately 1 mm.

An absorbent member c1 having the same structure as Example 1 was prepared, except that the topsheet (test material c1) was used, instead of the topsheet (test material 1).

The thus-obtained absorbent material c1 of 100×150 mm was placed on a moisture permeable sheet of the outer layer sheet (composite sheet of a non-woven fabric and a moisture permeable sheet) of 100×330 mm, thereby preparing a diaper test sample c1.

As in Example 1, also in the diaper test sample c1, the peripheral surface of the absorbent member c1 was covered with the outer layer sheet by approximately 10 mm, so that the absorbent member c1 pulp, absorbent polymer, and artificial urine poured in would not leak.

2. Skin Moisture Patch Test on Adult Forearm

Using the diaper test sample 1 of Example 1 and the diaper test sample c1 of Comparative Example 1 thus obtained, as patches, a model test was performed by the following procedures (1) to (3), to evaluate the skin moisture amount (skin moistening) on an adult forearm after patching.

(1) 20 ml of artificial urine kept at a temperature of 40° C. was poured into each of the diaper test samples 1 and c1 having the form of patches.

(2) The patch of the diaper test sample c1 of Comparative Example 1 was wrapped around one arm, and the patch of the diaper test sample 1 of Example 1 was wrapped around the other arm. At this time, the patches were wrapped so as to align the infused portion of the patch of the diaper test sample 1 or c1 with the measurement portion of the forearm, with the end portions being fixed in position by a tape. Further, so that no gap would be formed between the patch and the arm, an adhesive tape was attached to the periphery of the patch.

(3) After the lapse of 3 hours, the patch was removed and the skin moisture of the measurement portion immediately thereafter was measured using Corneometer MPA5 (trade name; manufactured by C+K GmbH).

(Results)

The skin moisture amount of the measurement portion before wrapping the patch of the diaper test sample was 30. In the case of the diaper test sample c1 of Comparative Example 1, the skin moisture amount after the patching was 82.4, which means an increase in skin moisture amount by 52.4. On the other hand, in the case of the diaper test sample 1 of Example 1, the skin moisture amount after the patching was 68.5, which means an increase in skin moisture amount by 38.5. The above-mentioned values were average values obtained from seven subjects, which also applies to the following.

As is known, when the above-mentioned value exceeds 75, a wet feel is produced on the skin, whereas when the value is 75 or less, a dry feel is produced. Thus, in the patch using the diaper test sample 1 of Example 1, it is found that there was no wet feel but a dry feel on the skin.

3. Evaluation of Suppression of Skin Texture Flattening at the Time of Skin Swelling by an Indirect Method (Replica Method)

For the skin surface after the patch test, a skin replica was prepared using a skin silicon impression agent (trade name: ABS-01 Sky Blue; manufactured by Asahibiomed Co., Ltd.), and the surface roughness Ra was measured using an analysis apparatus (Skin Visiometer SV500, (trade name), manufactured by C+K GmbH).

(Results)

In the skin replica using the patch of the diaper test sample c1 of Comparative Example 1, the surface roughness was 0.008 μm, whereas, in the skin replica using the patch of the diaper test sample 1 of Example 1, a rather rough surface roughness of 0.011 μm resulted, thus indicating suppression of the flattening of the skin texture.

It is known that skin texture is flattened through swelling of the skin with moisture. From this, it is found that, with the patch using the diaper test sample 1 of Example 1, the skin was less subject to swelling, as compared with the patch of the diaper test sample c1 of Comparative Example 1.

4. Evaluation of Horny Layer Thickness at the Time of Skin Swelling

The skin horny layer thickness after the patch test was measured by low coherence optical interferometry (optical coherence tomography) (trade name: Skin Dex 300; manufactured by ISIS).

(Results)

The skin horny layer thickness before wrapping the patch of the diaper test sample was 13.7 μm. The skin horny layer thickness when the patch of the diaper test sample c1 of Comparative Example 1 was wrapped was 19.2 μm, which means an increase in thickness by 9.4 μm. On the other hand, the skin horny layer thickness when the patch of the diaper test sample 1 of Example 1 was wrapped was 23.1 μm, which means an increase in thickness by 5.5 μm, It can be found from this that, with the patch of the diaper test sample 1 of Example 1, the increase in the thickness of the skin horny layer due to skin swelling was suppressed.

As is known, when the skin horny layer thickness increases due to skin swelling, the barrier function of the skin against external foreign matter diminishes. It can be seen that, with the patch using the diaper test sample 1 of Example 1, the skin barrier function diminished less easily than with the patch of the diaper test sample c1 of Comparative Example 1.

5. Panel Test.

The diaper test sample 1 of Example 1 was applied to infants, and evaluation test was conducted on a panel of 14 members (mothers with infants using disposable diapers). The opinion of the majority was used as the judgment results for the evaluation of the test example 1 as compared with the commercially available products they were currently using.

(1) The feel to the (hand) touch of the skin-contact surface of the test sample 1 was akin to that of cloth (fabric), and it was smooth and had a feel to the skin like that of cotton. In terms of appearance, it seemed highly-absorbable and free from backward flow of water.

(2) The diaper surface portion after urination was directly touched by the palm to check its feel. The result was that, in the test sample 1, the dry feel was higher as compared with the commercially available products, with less moisture adhering to the hand. Further, no moisture remained on the buttock skin of the infant, and stickiness due to urine, loose feces or the like was suppressed.

(3) With the diaper test sample 1, the amount of feces adhering to the buttocks of the infant was less than that in the case of the commercially available products. Rather, the feces adhered to the skin-contact surface of the diaper. Further, the feces thus adhering did not spread due to water absorption of the diaper test sample 1, but remained in the mud state solidified from the form as excreted. As a result, the feces adhering to the buttocks of the infant could be easily wiped away.

Example 2, Comparative Example 2

Example 2-1

Figure 15:
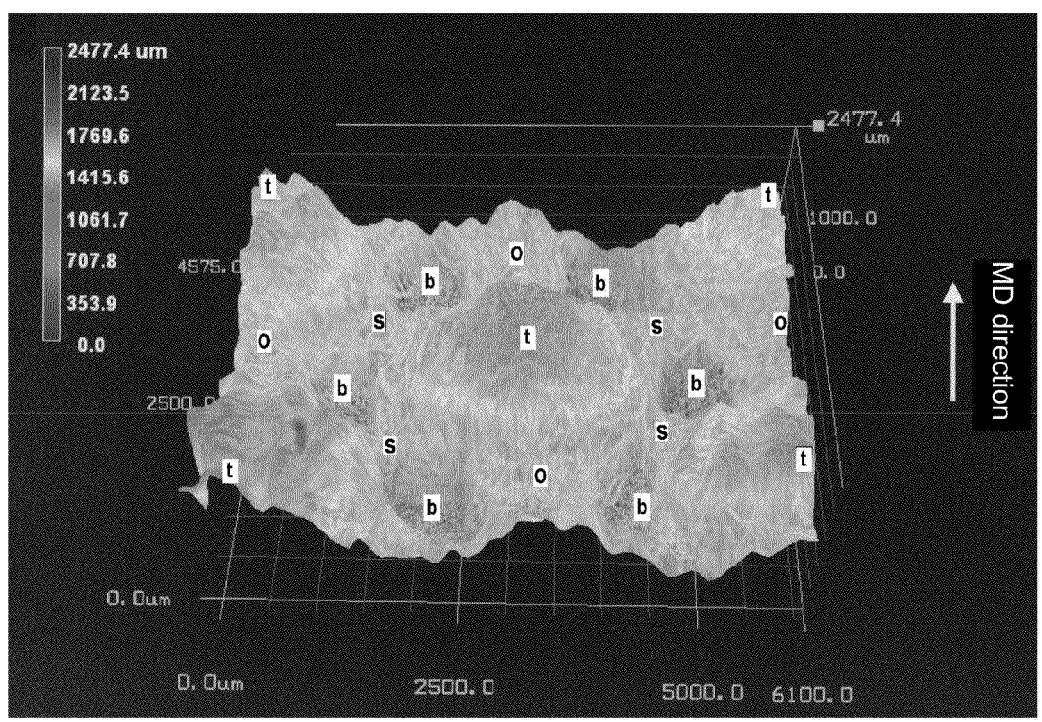
FIG. 15 is a surface configuration analysis chart in the form of a perspective view in which the surface configuration of a topsheet (test material 2-1) prepared as an example is measured and visualized with a surface profiler microscope.

As the non-woven fabric forming the upper layer sheet, use was made of an air-through non-woven fabric of basis weight 18 g/m², formed by overlaying a sheath/core-type conjugate fiber in a size and weight of 2.2 dtex×51 mm and 6 g/m², and a sheath/core-type conjugate fiber in a size and weight of 4.4 dtex×51 mm and 12 g/m², each of whose core was composed of polyethylene terephthalate and each of whose sheath was composed of polyethylene. The upper layer was bent in the MD direction through shaping and was increased in weight, so, after the shaping, it would become 22 g/m² (The speed at which the upper layer was paid out was increased by approximately 20% as compared with the speed at which the lower layer sheet was paid out). As the non-woven fabric forming the lower layer sheet, use was made of an air-through non-woven fabric of basis weight 18 g/m² formed by a sheath/core-type conjugate fiber in a size of 2.2 dtex×51 mm whose core was composed of polyethylene terephthalate and whose sheath was composed of polyethylene. By using these sheets, a topsheet (test material 2-1) according to the Third Embodiment was prepared, using the apparatus as illustrated in FIG. 6-1, with the first roll and the second roll in the tooth engagement pattern as illustrated in FIG. 6-3 (the interval 94: 3.2 mm; the interval 97: 1 mm; the interval 98: 2 mm; the length 99: 0.8 mm, the width 100: 1 mm; and the length 101: 0.8 mm). The thus-obtained topsheet (the test material 2-1) had a distinctive sheet configuration as illustrated in FIGS. 11 and 12. The height $h_t$ of the protrusions was approximately 1.7 to 2.1 mm, and the height $h_o$ of the ridge portions was approximately 0.6 to 1.0 mm. FIG. 15 is a surface configuration analysis chart in the form of a perspective view obtained by measuring and visualizing the surface configuration of the upper layer sheet side of this topsheet (the test material 2-1) with a surface profiler microscope (VHX-900 (trade name), manufactured by Keyence). In the figure, symbol "t" indicates the protrusions, symbol "b" indicates the recesses, symbol "o" indicates the ridge portions (connecting portions for being barriers), and symbol "s" indicates the small protrusions. The dimensional unit shown as "um" in the figure means "μm".

Example 2-2

As the non-woven fabric forming the upper layer sheet and the lower layer sheet, use was made of an air-through non-woven fabric of a sheath/core-type conjugate fiber of 2.2 dtex×51 mm in 18 g/m² whose core was composed of polyethylene terephthalate and whose sheath was composed of polyethylene: The upper layer was bent in the MD direction through shaping and was increased in weight, so, after the shaping, it would become 22 g/m² (The speed at which the upper layer was paid out was increased by approximately 20% as compared with the speed at which the lower layer sheet was paid out). From these sheets, a topsheet according to the Third Embodiment (test material 2-2) was prepared, using the apparatus as illustrated in FIG. 6-1, with the first roll and the second roll in the tooth engagement pattern as illustrated in FIG. 6-3 (the interval 94: 3.2 mm; the interval 97: 1 mm; the interval 98: 2 mm; the length 99: 0.8 mm, the width 100: 1 mm; and the length 101: 0.8 mm). The thus-obtained topsheet (the test material 2-2) had the distinctive sheet configuration as illustrated in FIGS. 11 and 12. The height $h_t$ of the protrusions was approximately 1.3 to 1.7 mm, and the height $h_o$ of the ridge portions was approximately 0.4 to 0.7 mm.

Comparative Example 2-1

Use was made of an air-through non-woven fabric, formed by overlaying: as the fiber web forming the upper layer sheet, a basis weight of 16 g/m² of a sheath/core-type conjugate fiber of 7.7 dtex×51 mm whose core was composed of polyethylene terephthalate and whose sheath was composed of polyethylene; and, as the fiber web forming the lower layer sheet, a basis weight of 24 g/m² of a sheath/core-type conjugate fiber of 3.3 dtex×51 mm whose core was composed of polyethylene terephthalate and whose sheath was composed of polyethylene. These sheets were overlaid and bonded together, thereby obtaining a topsheet (test material c2-1) for comparison. The thickness of the topsheet (the test material c2-1) was approximately 1 mm.

Comparative Example 2-2

A topsheet (test material c2-2) was obtained by superimposing and ultrasonic bonding together two sheets of air-through non-woven fabric of basis weight 20 g/m², as the non-woven fabrics forming the upper layer sheet and the lower layer sheet, with each non-woven fabric being formed of a sheath/core-type conjugate fiber of 2.2 dtex×51 mm whose core was formed of polyethylene terephthalate and whose sheath was formed of polyethylene. The thickness of the topsheet (the test material c2-2) was approximately 1 mm.

{Surface Layer Liquid Return Test}

The topsheets (test materials) whose weights had been measured were each placed on an absorbent material (a laminate formed of fluff pulp and high absorption polymer, with the basis weight of the pulp and of the polymer being 257 g/m², respectively). Then, 80 g of artificial urine was poured in at the central portion of the topsheet using a metering pump. After the pouring, the topsheet was left to stand for 10 minutes. After that, the weight of the topsheet was measured, and the weight before the evaluation was subtracted therefrom. The thus-obtained value was regarded as the surface layer liquid remaining amount of the non-woven fabric. When the liquid remaining amount is 300 mg or less, the requirement in terms of practical use is satisfied, and further when 150 mg or less, the requirement in terms of practical use can be satisfied at a higher level.

{Lateral Air-Permeability Test}

The topsheets (test materials) were each measured as follows for air passage volume in a direction parallel to the sheet surface under pressure of 35 g/m².

First, the thickness Th1 of the topsheet when a load of 35 g/m² was applied thereto was measured using a KES compression testing machine (KES FB-3 AUTO-A (trade name) with a circular contact portion (area: 2 cm²), manufactured by KATO TECH Co., Ltd.).

The topsheet whose thickness had been measured was held between a square first acrylic plate having at the center thereof a square opening one side of which was 10 mm (size: 50 mm×50 mm×3 mm) and a second acrylic plate that was the same as the first acrylic plate except that it had no opening, with the surface of the topsheet directed to the skin of the wearer being on the first acrylic plate side. This was set under the gasket of a Gurley tester (Type B) as defined in "Gurley tester method" of JIS P 8117, with the first acrylic plate side facing upwards, and compression was effected until the topsheet was reduced to the thickness Th1.

Then, the air was introduced via the opening into the central portion of the topsheet maintained at the thickness Th1, and the time period required for introducing 300 mL of the air was measured.

Then, the air introduction amount (cc) per unit area (1 cm²) of the opening×one second was calculated. The result of this lateral air permeability test indicates the ease with which the air moves on the topsheet, that is, the degree to which the topsheet is free from becoming steamy. When the lateral air permeability amount is 30 cc/sec or more, the requirement in terms of practical use is satisfied, and further when 70 cc/sec or more, the requirement in terms of practical use can be satisfied at a higher level.

{KES Thickness}

The topsheets (test materials) were each measured for thickness under a load of 0.5 g/cm² and a load of 50 g/cm² applied thereto (the sample thickness obtained by adding the lower layer sheet thickness to the height $h_t$ of the protrusions) using a KES compression testing machine (KES FB-3 AUTO-A (trade name) with a circular contact portion (area: 2 cm²), manufactured by KATO TECH Co., Ltd.). The larger the value of this thickness is, the more satisfactory cushioning property is maintained when the diaper is actually worn. More specifically, the requirement in terms of practical use can be satisfied when the KES thickness is 1.2 or more under the load condition of 0.5 g/cm², when the KES thickness is 0.8 or more under the load condition of 20 g/cm², and when the KES thickness is 0.5 or more under the load condition of 50 g/cm².

{Compressive Hardness (KES) Test}

The topsheets (test materials) were each measured for compressive hardness under a load of 50 g/cm².

Compression characteristic measurement was performed on the topsheet by pressurizing it to a load of up to 50 g/cm², using a KES compression testing machine (KES FB-3 AUTO-A (trade name) with a circular contact portion (area: 2 cm²), manufactured by KATO TECH Co., Ltd.). In the above compressive hardness (KES) test, the LC value indicates compressibility with small force. When it is 0.75 or less, the requirement in terms of practical use can be satisfied. The WC value indicates softness. When it is 0.5 gf·cm/cm² or more, the requirement in terms of practical use is satisfied. When it is 1.0 gf·cm/cm² or more, the requirement in terms of practical use can be satisfied at a higher level. The RC value indicates compression recovery property. When it is 30% or more, the requirement in terms of practical use can be satisfied at a higher level.

{Test on Drape Characteristic, KES Bending Property B'}

The topsheets (test materials) were each measured for bending moment when a fixed curvature (±2.5 cm$^{-1}$) was imparted thereto.

The topsheet was cut into a 20 cm×10 cm (MD×CD) shape, to thereby give a specimen. Measurement was performed on the bending moment when a fixed curvature (±2.5 cm$^{-1}$) was imparted to the thus-obtained specimen in the MD direction and the CD direction, using a KES bending tester (KES FB-2 AUTO-A (trade name), manufactured by KATO TECH Co., Ltd.). The bending moment value when the curvature is ±2.5 cm$^{-1}$ is designated to "B'".

In the above test on drape characteristic and KES bending property B', the smaller the value is, the easier it is for the sheet to be bent. When the value is 0.35 gf·cm$^2$/cm or less in one direction (MD direction), the requirement in terms of practical use is satisfied. When 0.2 gf·cm$^2$/cm or less, the requirement in terms of practical use is satisfied at a higher level. When 0.20 gf·cm$^2$/cm or less in the other direction (CD direction), the requirement in terms of practical use is satisfied.

{Presence or Absence of Buckling (MD Folded-in-Half Portion) Test}

The topsheets (test materials) were each folded in half (in MD direction) using a ruler as the reference point and the state of the folded-in-half when opened was checked. When the evaluation [criteria as described in the below] is "∘" or better, the requirement in terms of practical use is satisfied. When the evaluation is "∘∘" or better, the requirement in terms of practical use is satisfied at a higher level.

"x": There are a plurality of folds, wrinkles, and corners, with the fold feeling hard.

"Δ": There are folds with a plurality of wrinkles remaining, and a little hardness of the folds is felt.

"∘": While there are folds, there are no wrinkles. Hardness of the folds is scarcely felt.

"∘∘": There are no folds, with the original state being maintained. Hardness of the folds is not felt at all.

{Feel-to-the-Touch Test}

The topsheet of a diaper which had undergone the surface layer remaining liquid amount measurement test, was directly touched with the palm, to check the feel to the touch. The surface of the topsheet (the upper layer surface) before being incorporated into the diaper was directly touched with the palm, and its feel was judged according to the following criteria. The judgment was made by three or more people, and the opinion of the majority was regarded as the judgment result. When the opinions differed from people to people, the opinion in-between was adopted as the judgment result. When the evaluation is "∘" or better, the requirement in terms of practical use is satisfied. When the evaluation is "∘∘" or better, the requirement in terms of practical use is satisfied at a higher level.

"x": Hard. There is a feel of resistance (rough feel).

"Δ": Somewhat hard. There is a little feel of resistance (rough feel).

"∘": Somewhat soft. There is a somewhat smooth feel.

"∘∘": Soft, and there is a smooth feel.

TABLE 1

| | | Test material 2-1 | Test material 2-2 | Test material c2-1 | Test material c2-2 |
|---|---|---|---|---|---|
| Weight (g/cm$^2$) | | 42.1 | 41.6 | 40.8 | 39.5 |
| Surface liquid return (mg) | | 130 | 154 | 390 | 185 |
| Lateral air-permeability (cc/sec) | | 84 | 79 | 28 | 20 |
| KES thickness (mm) | 0.5 g/cm$^2$ | 1.87 | 1.49 | 0.93 | 0.83 |
| | 20 g/cm$^2$ | 1.01 | 0.92 | 0.45 | 0.34 |
| | 50 g/cm$^2$ | 0.65 | 0.53 | 0.38 | 0.28 |
| Compressive hardness | LC | 0.60 | 0.71 | 0.32 | 0.29 |
| | WC | 1.81 | 1.71 | 0.44 | 0.40 |
| KES | RC | 46.4 | 41.6 | 66.1 | 62.0 |
| Drape characteristics | MD | 0.185 | 0.196 | 0.366 | 0.136 |
| | CD | 0.109 | 0.119 | 0.133 | 0.050 |
| KES bending property B' | | | | | |
| Buckling (MD folded-in-half portion) | | ∘∘ | ∘∘ | Δ | ∘ |
| Feel to the touch | | ∘∘ | ∘∘ | Δ | ∘ |

From the above results, it can be seen that, as compared with the Comparative Examples (the test materials c2-1 and c2-2), the topsheets according to the Third Embodiment (the test materials 2-1, 2-2) exhibited quite higher surface liquid return property and lateral air permeability. Further, it can be seen that, to the Comparative Examples (the test materials c2-1 and c2-2), the topsheets according to the Third Embodiment (the test materials 2-1, 2-2) exhibited superior results in the property evaluations of sheets (KES thickness test, compressive hardness test, drape characteristics test, presence or absence of buckling test, and feel-to-the-touch test). Further, it can also be seen that the topsheets according to the Third Embodiment (the test materials 2-1, 2-2) easily conforms to the skin contour, and offers a soft and smooth texture.

Example 3

As the non-woven fabric forming the first sheet, a two-layer sheet (upper layer sheet) was provided, which was formed by bonding together a first layer of an air-through non-woven fabric of basis weight 6 g/m$^2$ that was formed of a sheath/core-type conjugate fiber of 2.2 dtex whose core was composed of polyethylene terephthalate and whose sheath was composed of polyethylene, and a second layer of an air-through non-woven fabric of basis weight 12 g/m$^2$ that was formed of a sheath/core-type conjugate fiber of 4.4 dtex whose core was composed of polyethylene terephthalate and whose sheath was composed of polyethylene. The thickness of the upper layer sheet was 0.6 mm. As the non-woven fabric forming the lower layer sheet, use was made of an air-through non-woven fabric of basis weight 18 g/m$^2$ that was formed of a sheath/core-type conjugate fiber of 2.2 dtex whose core was composed of polyethylene terephthalate and whose sheath was composed of polyethylene. The thickness of the lower layer sheet was 0.6 mm. By using these sheets, a topsheet (test material 3-1) according to the Fourth Embodiment was prepared, using the apparatus illustrated in FIG. 6-1. In the thus-obtained sheet (test material 3-1), the height $h_t$ of the protrusions was 1.4 mm, the width $w_t$ of the protrusions in line with the X-direction was 4.0 mm, and the width $w_b$ of bonding portions (recesses) was 1.0 mm.

Topsheets (test materials 3-2 through 3-8) were prepared in the same as the test material 3-1, except that the fineness of the fibers used in the upper layer sheet and the lower layer sheet, the basis weight of the sheets, and the air-through temperature of the upper layer sheet first layer were changed as shown in Table 2. In the table, symbol "x" indicates preparation of a first layer of a one-layer structure using solely the layer as given as the outer layer, without using any inner layer.

Disposable diapers were prepared using the sheets (test materials) as the topsheets, with the upper layer sheet on the skin-contact surface side. As the absorbent member, use was made of a laminate fiber body formed of fluff pulp and high absorption polymer. The basis weight of the pulp was 257 g/m², and the basis weight of the polymer was 257 g/m². Each sheet test material was arranged on the surface of this absorbent member. As an external capsule member, use was made of a moisture permeable film of basis weight 20 g/m². Using the disposable diapers thus obtained, the following tests were conducted on each test material. The results are shown in Table 2.

{Surface Layer Liquid Remaining Amount Measurement test}

Each diaper was placed on a horizontal stand so that the topsheet thereof faced upwards. Thereon, a rectangular frame of an inner size of 20 cm×10 cm was placed. The inner side of the frame was traced with an oil-based ink pen, transcribing the inner side configuration of the frame onto the topsheet. Then, 200 g of artificial urine was uniformly poured into the frame. After the pouring, the sheet was left to stand for 10 minutes. The frame was removed after 1 minute after the pouring had passed. After being left to stand for 10 minutes, the topsheet was cut along the transcribed frame configuration, and the mass thereof was measured. Then, the thus-cut out non-woven fabric was held between kitchen paper sheets, and, in this state, it was caused to make one pass and return through a mangle, thereby causing the artificial urine to be absorbed in the kitchen paper sheets. This operation was conducted twice. The mass of the non-woven fabric after the absorption of artificial urine was measured again, and the mass was subtracted from the mass of the non-woven fabric obtained first through measurement. The value was regarded as the surface layer liquid remaining amount of the non-woven fabric. The smaller the value is, the higher the level at which the requirement of the wearer can be satisfied.

{Feel-to-the-Touch Test}

The topsheet of a diaper which had undergone the surface layer remaining liquid amount measurement test, was directly touched with the palm, to check the feel to the touch.

The surface of the topsheet (the upper layer surface) before being incorporated into the diaper was directly touched with the palm, and its feel was judged according to the following criteria. The judgment was made by three or more people, and the opinion of the majority was regarded as the judgment result. When the opinions differed people to people, the opinion in-between was adopted as the judgment result. "x": Hard, and there is a feel of resistance (rough feel). "Δ": Somewhat hard, and there is a little feel of resistance (rough feel). "○": Somewhat soft, and there is a somewhat smooth feel. "○○": Soft, and there is a smooth feel.

{Configuration Stability Measurement test}

The topsheets (test materials) were subjected to measurement on the sample thickness as obtained by adding the thickness of the lower layer sheet to the height $h_r$ of the protrusions (FIG. 2) when a load of 2.5 kPa was applied thereto, using a KES Compressor (KES FB-3 AUTO-A (trade name) with a circular contact portion (area: 2 cm²). The larger the value of this thickness is, the more satisfactory is the cushioning property maintained when the diaper is actually worn. The larger this value is, the higher the level at which the requirement of the wearer can be satisfied.

{Edge Angle Measurement}

The angle made by a straight line obtained by cutting the protrusion 4 from the apex thereof with a razor edge in a direction parallel to the X-direction and extending from the apex parallel to the X-direction, and by a straight line extending from the wall portion 4c, was measured as the edge angle (see FIGS. 1, 2). The larger this value is, the more satisfactory is the feel to the touch that can be experienced by the wearer.

TABLE 2

| | | | Test material | | | | | | | |
|---|---|---|---|---|---|---|---|---|---|---|
| | | | 3-1 | 3-2 | 3-3 | 3-4 | 3-5 | 3-6 | 3-7 | 3-8 |
| Upper layer sheet | First layer | Resin | PET/PE | ← | ← | ← | ← | ← | ← | ← |
| | | Fineness | Coaxial | ← | ← | ← | Coaxial | ← | Offset | Coaxial |
| | | dtex | 2.2 | | | | 2.2 | | 4.4 | 5.6 |
| | | Basis weight g/m² | 6 | 9 | 6 | 9 | 18 | 18 | 18 | 18 |
| | Second layer | Resin | PET/PE | ← | ← | ← | | | | |
| | | Fineness | Offset | ← | Coaxial | ← | | | | |
| | | dtex | 4.4 | | 5.6 | | | | | |
| | | Basis weight g/m² | 12 | 9 | 12 | 9 | | | | |
| Lower layer sheet | Resin | | PET/PE | ← | ← | ← | ← | ← | ← | ← |
| | Fineness dtex | | 2.2 | ← | ← | ← | ← | ← | ← | ← |
| | Basis weight g/m² | | 18 | ← | ← | ← | ← | ← | ← | ← |
| Air-through temperature ° C. | | | 129 | ← | ← | ← | 133 | 129 | 133 | 133 |
| Configuration stability (thickness mm) | | | 0.62 | 0.60 | 0.66 | 0.61 | 0.58 | 0.53 | 0.68 | 0.75 |
| Surface layer liquid remaining amount g | | | 0.11 | 0.12 | 0.17 | 0.18 | 0.27 | 0.25 | 0.11 | 0.17 |
| Feel to the touch | | | ○○ | ○○ | ○ | ○ | ○ | ○○ | Δ | Δ |
| Edge angle ° | | | 110 | 113 | 115 | 120 | 93 | 99 | 125 | 132 |

As can be seen from the results shown in Table 2, the test materials 3-1 through 3-8 satisfied to a sufficient degree the requirement level in terms of each evaluation item of the topsheet. Above all, it can be seen that the topsheets according to the Fourth Embodiment (test materials 3-1 through 3-4), in which the upper layer sheet was of a two-layer structure, satisfied the requirement in terms of practical use at a higher level in all of the items of protrusion configuration stability, surface layer liquid remaining suppression effect, and feel to the touch. It can be seen, in particular, that, by adjusting the fineness of the first layer and the second layer forming the upper layer sheet, it is possible to attain a very satisfactory feel to the touch and to remarkably enhance the surface layer liquid remaining suppression effect (test materials 3-1, 3-2).

Example 4

Example 4-1

A topsheet according to the First Embodiment, in which an upper layer and a lower layer each of which was of a one-layer structure were bonded together in a 6-point seal pattern, was prepared using the manufacturing apparatus as illustrated in FIG. 6-1, and a diaper for infants (test material 4-1) was prepared using this topsheet. The fineness of the fibers of the upper layer of the topsheet was 2.2 dtex, and the fineness of the fibers of the lower layer thereof was 2.2 dtex. The inter-fiber interval in the obtained upper layer was 100 µm, and the inter-layer interval of the lower layer was 55 µm. The thickness of the upper layer of the topsheet was approximately 70 µm, and the thickness of the lower layer thereof was approximately 50 µm. The interval between the adjacent protrusions was approximately 2.5 mm, and the height of the protrusions was approximately 1.3 mm.

With respect to the test material 4-1, evaluation was made by six panel members (mothers with infants using disposable diapers) on the appearance and the feel to the touch of the topsheet side (diaper inner side) of the test material. The results were that the test material was satisfactory in terms of practical use regarding the appearance (softness, smoothness, and dry feel) on the skin-contact surface side of the diaper, where the topsheet was located.

Example 4-2

A topsheet according to the Fourth Embodiment was prepared in the same manner as the test material 4-1, except that the upper layer of the topsheet was of a two-layer structure having a first layer and a second layer, and a diaper for infants (test material 4-2) was prepared using this topsheet. The fineness of the fibers of the first layer of the upper layer of the topsheet was 2.2 dtex, the fineness of the fibers of the second layer was 4.4 dtex, and the fineness of the fibers of the lower layer was 2.2 dtex. The inter-fiber interval in the first layer of the upper layer obtained was 90 µm, the inter-fiber interval of the second layer was 140 µm, and the inter-fiber interval of the lower layer was 55 µm. The thickness of the upper layer, the thickness of the lower layer, the interval between the adjacent protrusions, and the protrusion height of the topsheet of the test material 4-2 were approximately the same as those of the test material 4-1.

A panel evaluation test similar to the one described above was made on the test material 4-2. The results were that the diaper of the test material 4-2 was of the level of satisfactory or very satisfactory in terms of practical use regarding the appearance (softness, smoothness, and dry feel) as seen from the skin-contact surface side where the topsheet was located. Further, the feel to the touch was remarkably improved as compared with the test material 4-1, and the feel to the touch of the topsheet portion of the diaper of the test material 4-2 was evaluated of the level as very satisfactory in terms of practical use regarding all the evaluation items of softness, smoothness, and dry feel.

Example 5

Test Material 5-1

Using the manufacturing apparatus illustrated in FIG. 6-1, a topsheet according to the Fourth Embodiment was pre-pared, in which an upper layer sheet having a first layer on the skin-contact surface side and a second layer on the non-skin-contact surface side, and a lower layer sheet, were bonded together in a 6-point seal pattern. Then, a diaper for infants (test material 5-1) was prepared, in which this topsheet was overlaid on an absorbent member. As the absorbent member, use was made of one obtained by wrapping a composite laminate fiber body of fluff pulp and high absorption polymer in tissue. The basis weight of the fluff pulp was 215 g/m$^2$, and the basis weight of the high absorption polymer was 300 g/m$^2$. At this time, the non-skin-contact surface (lower surface) of the topsheet and the skin-contact surface (upper surface) of the absorbent member were not bonded together, with the two being fixed to the back sheet while bonded solely at the edge portions. The fineness of the fibers of the first layer of the upper layer sheet of the topsheet was 2.2 dtex, the fineness of the fibers of the second layer thereof was 4.4 dtex, and the two layers were integrated into a sheet through hot air treatment after superimposing the upper layer sheet and the lower layer sheet one upon the other. The fineness of the fibers of the lower layer sheet of the topsheet was 2.2 dtex. The thickness of the upper layer sheet of the obtained topsheet was approximately 70 µm, and the thickness of the lower layer sheet thereof was approximately 50 µm. The width $w_t$ of the protrusions was approximately 4.0 mm, the width $w_b$ of the recesses was approximately 1.0 mm, and the height $h_t$ of the protrusions was approximately 1.4 mm.

Test Material 5-2

A diaper for infants (test material 5-2) in which a sublayer was disposed between the topsheet and the absorbent member was prepared in the same manner as the test material 5-1. As the absorbent member, use was made of one obtained by wrapping a composite laminate fiber body of fluff pulp and high absorption polymer in tissue. The basis weight of the fluff pulp was 215 g/m$^2$, and the basis weight of the high absorption polymer was 300 g/m$^2$. At this time, the stacking (lamination) interfaces of the topsheet, the sublayer, and the absorbent member were not bonded together, and they were fixed to a back sheet while bonded together solely at the edge portions. The sublayer was of a two-layer structure, and it consisted of a sublayer upper layer on the skin-contact surface side and a sublayer lower layer, which were integrated through bonding by hot air treatment after superimposing the upper layer and the lower layer one upon the other. The fineness of the fibers of the sublayer upper layer was 7.8 detex, and the fineness of the fibers of the sublayer lower layer was 3.3 dtex. The thickness of the sublayer was approximately 0.85 mm.

Test Material 5-3

A diaper for infants (test material 5-3) was prepared in the same manner as the test material 5-1, except that the fineness of the fibers forming the second layer of the upper layer sheet of the topsheet was changed to 2.2 dtex. The thus-obtained test material was subjected to measurement on the surface material liquid remaining amount and the surface material liquid diffusion area. The thickness of the upper layer, the thickness of the lower layer, the width of the protrusions, the width of the recesses, and the height of the protrusions of the topsheet of the test material 5-3 were approximately the same as those of the test material 5-1.

Test Material 5-4

A diaper for infants (test material 5-4) was prepared in the same manner as the test material 5-2, except that the fineness of the fibers forming the second layer of the upper layer sheet of the topsheet was changed to 2.2 dtex. The thus-obtained test material was subjected to measurement on the surface material liquid remaining amount and the surface material liquid diffusion area. The thickness of the upper layer, the thickness of the lower layer, the width of the protrusions, the width of the recesses, and the height of the protrusions of the topsheet of the test material 5-4 were approximately the same as those of the test material 5-1.

Test Material 5-5

A diaper for infants (test material 5-5) was prepared in the same manner as the test material 5-4, except that the fineness of the fibers of the sublayer upper layer sheet was changed to 3.3 dtex, and that the fineness of the fibers of the sublayer lower layer was changed to 7.8 dtex. The thus-obtained test material was subjected to measurement on the surface material liquid remaining amount and the surface material liquid diffusion area. The thickness of the sublayer of the test material 5-5 was approximately the same as that of the test material 5-4.
{Surface Material Liquid Remaining Amount and Surface Material Liquid Diffusion Area Testing Methods}

A topsheet whose weight had previously been measured was used as the test material. The test material was placed on a horizontal stand so that the topsheet faced upwards, and then 80 g of artificial urine was poured at one time into substantially the center of the absorbent member at the rate of 5 g/sec. After the pouring-in, the test material was left to stand still for 10 minutes, and then a transparent film was placed on the topsheet. The periphery of the wet portion of the topsheet was traced over the transparent film with an oil-based ink pen, and the area of the figure thus traced was measured, to thereby obtain the surface material liquid diffusion area. Then, solely the topsheet was taken out from the test material, to measure the weight thereof, and the difference between this weight and the weight of the topsheet before the stacking on the test material was calculated, thereby obtaining the surface material liquid remaining amount. The less the amount of the surface remaining liquid is and the smaller the surface material liquid diffusion area is, the higher the level at which the requirement in terms of practical use can be satisfied.

The evaluation results are collectively shown in Table 3. As can be seen from the table, as compared with the case of the test material 5-3, in the test material 5-1, the surface material liquid remaining amount and the surface material liquid diffusion area were both kept at a lower level. Further, it can be seen that, as compared with the cases of the test materials 5-4 and 5-5, in the test material 5-2, the surface material liquid remaining amount was kept at a remarkable lower level. As can be seen, by thus adjusting the thickness of the fibers forming the upper layer sheet (first layer, second layer) and the lower layer sheet, and the sublayer of the surface sheet, it is possible to keep the surface material liquid remaining amount and the surface material liquid diffusion area at a still lower level.

TABLE 3

|  |  | Test material | | | | |
|---|---|---|---|---|---|---|
|  |  | 5-1 | 5-2 | 5-3 | 5-4 | 5-5 |
| Upper layer sheet | First layer | 2.2 | 2.2 | 2.2 | 2.2 | 2.2 |
|  | Second layer | 4.4 | 4.4 | 2.2 | 2.2 | 4.4 |
| Lower layer sheet |  | 2.2 | 2.2 | 2.2 | 2.2 | 2.2 |

TABLE 3-continued

|  |  | Test material | | | | |
|---|---|---|---|---|---|---|
|  |  | 5-1 | 5-2 | 5-3 | 5-4 | 5-5 |
| Sublayer | First layer |  | 7.8 |  | 7.8 | 3.3 |
|  | Second layer |  | 3.3 |  | 3.3 | 7.8 |
| Surface material liquid remaining amount (g) |  | 0.03 | 0.06 | 0.05 | 0.11 | 0.13 |
| Surface material liquid diffusion area (cm$^2$) |  | 77 | 68 | 103 | 66 | 81 |

As is shown from the above results, the shaped sheet of the present invention exhibits a satisfactory feel to the touch and cushioning feel when applied to an absorbent article, and further, can draw liquid quickly from the skin-contact surface side to the non-skin-contact surface side. Further, the shaped sheet of the present invention enables quick transfer of liquid to the absorbent member side without allowing the liquid to stay on the sheet surface, and makes it possible to keep the surface material liquid remaining amount and the surface material liquid diffusion area at a quite low level, thus it exhibits such excellent effects of maintaining a dry feel to the touch and cleanliness.

INDUSTRIAL APPLICABILITY

The shaped sheet of the present invention can be used as an absorbent article sheet, a hook engagement sheet disposed where engagement with a mechanical hook is required, a cleaning sheet, a skin wiping sheet, a wound protecting sheet, a cooking sheet, an oil absorbing sheet for cooking, or the like, or as a sheet material forming these. Above all, the shaped sheet of the present invention can be favorably used, for example, as a topsheet for an absorbent article, such as a disposable diaper, a sanitary napkin, and a panty liner.

Having described our invention as related to the present embodiments, it is our intention that the invention not be limited by any of the details of the description, unless otherwise specified, but rather be construed broadly within its spirit and scope as set out in the accompanying claims.

The invention claimed is:

1. A shaped sheet formed of fibers, comprising:
a plurality of protrusions, connecting portions, and recesses, on one surface side of the shaped sheet;
wherein the connecting portions are barriers and connect the protrusions to one another with no intervening recesses;
wherein the recesses are positioned between the protrusions and avoid the connecting portions;
wherein six recesses surround each of said protrusions; and
wherein the shaped sheet comprises: an upper layer sheet having the protrusions; a flat lower layer sheet arranged on a surface side opposite to the protrusions protruding, the lower layer sheet being bonded with the upper layer sheet via at least a part of the recesses of the upper layer sheet.

2. The shaped sheet according to claim 1, wherein the recesses have a fiber density higher than the fiber density of the connecting portion, the connecting portion having a fiber density higher than a fiber density of the protrusion.

3. The shaped sheet according to claim 1, wherein each of the protrusions is connected to all the protrusions adjacent thereto via the connecting portions.

4. The shaped sheet according to claim 1, wherein the connecting portions are of two kinds: a first connecting portion and a second connecting portion, the second connecting portion having a height lower than a height of the first connecting portion.

5. The shaped sheet according to claim 1, wherein each of the protrusions has an inner space.

6. The shaped sheet according to claim 1, wherein the protrusions are arranged in a staggered manner, said six recesses surrounding the protrusion are positioned so as to form a hexagon by connecting the centers of the six recesses,
wherein the staggered manner means a state in which the protrusions are provided in a plurality of rows and, when the protrusions of each row are projected in a direction orthogonal to the row, the projected images of the protrusions of the adjacent row are arranged between the projected images of the protrusions of a specific row.

7. The shaped sheet according to claim 1, wherein the protrusions are arranged in a staggered manner and each of the protrusions has an inner space, and the protrusions are connected to one another via the connecting portions to form protrusion rows, in which the connecting portion has a width narrower than a width of the protrusion with respect to a direction orthogonal to the connecting direction of the row, and
wherein the protrusion rows are arranged in parallel so that groove portions arranged between the rows are broken-line-shaped, and the recesses are provided in the groove portions with positioning the recesses on both sides of the connecting portions.

8. The shaped sheet according to claim 1, wherein a tunnel shaped space is provided within the connecting portion, an inner space is provided in the protrusion, and the tunnel space interconnects the inner spaces of the protrusions to one another.

9. The shaped sheet according to claim 1, wherein the protrusion and the six recesses surrounding the protrusion constitute a pattern element, and a plurality of the pattern elements are repeatedly formed in the shaped sheet while sharing at least two recesses of the each pattern element.

10. The shaped sheet according to claim 1, wherein the upper layer sheet comprises a first layer and a second layer, the second layer being formed of a fiber and arranged on a side of the lower layer sheet, the first layer being formed of a fiber and arranged on an outer side of the second layer, and the fiber forming the first layer has a fiber thickness thinner than a fiber thickness of the fiber forming the second layer.

11. The shaped sheet for an absorbent article according to claim 10, wherein the fiber forming the second layer in the upper layer sheet has a fiber thickness thicker than a fiber thickness of the fiber forming the lower layer sheet.

12. The shaped sheet according to claim 11, wherein a ratio of a fineness $E_{1d}$ of the fiber forming the first layer in the upper layer sheet to a fineness $E_{2d}$ of the fiber forming the second layer, $E_{1d}/E_{2d}$, is in the range of 10 to 70%, and wherein a ratio of the fineness $E_{2d}$ of the fiber forming the second layer in the upper layer sheet to a fineness $E_{3d}$ of the fiber forming the lower layer sheet, $E_{2d}/E_{3d}$, is in the range of 150 to 800%.

13. An absorbent article, comprising the shaped sheet according to claim 1 being located near at least an excretion region, with the surface side of having the protrusions directed toward a skin surface side.

14. The absorbent article according to claim 13, wherein the shaped sheet is provided on the skin surface side of an absorbent member and a sublayer is provided between the shaped sheet and the absorbent member.

15. The shaped sheet according to claim 1, wherein a six-point recess surrounding the protrusion constitutes a pattern element, and a plurality of the pattern elements are repeatedly formed in the shaped sheet in accordance with the following manner when the position of the recesses are referred to in a row number and a column number;
wherein points (1, 2), (1, 4), (3, 1), (3, 5), (5, 2), and (5, 4) constitute the first element, here, the values in the parentheses indicate (row number, column number);
wherein the adjacent second element on the right-hand side is formed by six points (1, 8), (1, 10), (3, 7), (3, 11), (5, 8), and (5, 10);
wherein the third element below the first element shares the two points (5, 2) and (5, 4) with the first element, and includes points (7, 1), (7, 5), (9, 2), and (9, 4); and
wherein the fourth element on the right-hand side of the third element shares the points (3, 5), (3, 7), (5, 4), (7, 5), and (5, 8) with one or another of the first through third elements, and includes point (7, 7).

16. The shaped sheet according to claim 15, in the pattern element constituted of the six recesses surrounding the protrusion, the connecting portion is positioned in the following manner;
wherein the central point β of the first element constitutes the protrusion and the first connecting portions are disposed at positions γ between the recesses in front of and behind the protrusion, and the second connecting portions are disposed at positions ε between the other recesses;
wherein the protrusion is also disposed at the position β at the center of the third element, the protrusion is connected to the protrusion of the first element through the first connecting portions formed at the positions γ between the recesses, and thereby the column extending at the column 3 (coordinate) formed by the positions β and γ constitutes a protrusion row in the sheet; and
wherein another protrusion rows are repeated at column 6 (coordinate), column 9 (coordinate), and the protrusions spread out in a plane direction in the staggered manner.

17. The shaped sheet according to claim 1,
wherein the connecting portion is defined in a first connecting portion and a second connecting portion lower in height than the first connecting portion;
wherein the protrusions and the first connecting portions are connected and positioned in a cross section at a cross section line of being along a machine direction and passing the tops of the protrusions;
wherein the protrusions and the first connecting portions are positioned with the recesses interposed between the protrusions and the first connecting portion in a cross section at a cross section line of being orthogonal to the machine direction and passing the tops of the protrusions; and
wherein the protrusions and the second connecting portions are connected and positioned in a cross section at a cross section line of being diagonally crossing the machine direction and passing the protrusions and the second connecting portions.

* * * * *